(12) United States Patent
Veryasov et al.

(10) Patent No.: US 12,049,435 B2
(45) Date of Patent: Jul. 30, 2024

(54) PROCESS TO CONDUCT ENDOTHERMIC DIRECT PYROLYSIS OF METHANE IN A FLUIDIZED BED REACTOR

(71) Applicant: TOTALENERGIES ONETECH, Courbevoie (FR)

(72) Inventors: Gleb Veryasov, Nivelles (BE); Nikolai Nesterenko, Nivelles (BE); Walter Vermeiren, Houthalen (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/017,360

(22) PCT Filed: Jul. 27, 2021

(86) PCT No.: PCT/EP2021/071051
§ 371 (c)(1),
(2) Date: Jan. 20, 2023

(87) PCT Pub. No.: WO2022/023368
PCT Pub. Date: Feb. 3, 2022

(65) Prior Publication Data
US 2023/0271899 A1 Aug. 31, 2023

(30) Foreign Application Priority Data

Jul. 28, 2020 (EP) .................................... 20315370

(51) Int. Cl.
*C01B 32/05* (2017.01)
*B01J 6/00* (2006.01)
*B01J 8/42* (2006.01)
*C07C 2/80* (2006.01)

(52) U.S. Cl.
CPC ................ *C07C 2/80* (2013.01); *B01J 6/008* (2013.01); *B01J 8/42* (2013.01); *C01B 32/05* (2017.08); *B01J 2208/00398* (2013.01); *B01J 2208/00415* (2013.01); *B01J 2208/0053* (2013.01); *C01B 2203/0277* (2013.01); *C01B 2203/1241* (2013.01)

(58) Field of Classification Search
CPC ...................................................... C01B 32/05
See application file for complete search history.

(56) References Cited

U.S. PATENT DOCUMENTS

| 2,982,622 | A | 5/1961 | Jahnig et al. |
| 3,254,957 | A | 6/1966 | Meiers et al. |
| 3,399,969 | A * | 9/1968 | Bokros ................... C01B 32/00 |
| | | | 423/454 |
| 6,814,857 | B1 * | 11/2004 | Gu ............................. B01J 8/12 |
| | | | 422/219 |
| 2013/0006024 | A1 | 1/2013 | Kurukchi et al. |

FOREIGN PATENT DOCUMENTS

WO 2019/145279 A1 8/2019

OTHER PUBLICATIONS

International Search Report dated Oct. 27, 2021 issued in corresponding International Application No. PCT/EP2021/071051.
International Preliminary Report on Patentability dated Jul. 26, 2022 issued in corresponding International Application No. PCT/EP2021/071051.

* cited by examiner

*Primary Examiner* — Stuart L Hendrickson
(74) *Attorney, Agent, or Firm* — Nath, Goldberg & Meyer; Joshua B. Goldberg

(57) ABSTRACT

The disclosure relates to a process to perform an endothermic methane pyrolysis reaction, said process comprising the steps of providing at least one fluidized bed reactor comprising at least two electrodes; and a bed comprising particles, wherein the particles are put in a fluidized state by passing upwardly through the said bed a fluid stream, to obtain a fluidized bed; heating the fluidized bed to a temperature ranging from 500° C. to 1200° C. to conduct the endothermic methane pyrolysis reaction; wherein the particles of the bed comprise electrically conductive particles and particles of a catalytic composition; wherein at least 10 wt. % of the particles are electrically conductive particles and have a resistivity ranging from 0.001 Ohm·cm to 500 Ohm·cm at 800° C. and wherein the step of heating the fluidized bed is performed by passing an electric current through the fluidized bed.

11 Claims, 6 Drawing Sheets

PROCESS TO CONDUCT ENDOTHERMIC DIRECT PYROLYSIS OF METHANE IN A FLUIDIZED BED REACTOR

This is a National Phase Application filed under 35 U.S.C. 371 as a national stage of PCT/EP2021/071051, filed Jul. 27, 2021, an application claiming the benefit of European Application No. 20315370.5, filed Jul. 28, 2020, the content of each of which is hereby incorporated by reference in its entirety.

TECHNICAL FIELD

The present disclosure relates to a process for performing endothermic direct pyrolysis of methane in a fluidized bed reactor wherein the reaction is performed without the need of an external heating device in the said fluidized bed reactor. The present disclosure aims to contribute to the replacement of the use of fossil carbon-based fuels heating devices. The present disclosure relates to the electrification of the chemical industry.

TECHNICAL BACKGROUND

Climate change and ongoing energy transition make it mandatory to replace fossil carbon-based fuels in chemical production and recycled processes with a more environmentally friendly decarbonized source of energy. Transforming natural gas into hydrogen and valuable chemicals requires elevated temperatures, often higher than 800° C. and even up to 1200° C. and are often endothermic. The energy needed is, therefore, high and not often environmentally friendly, as is demonstrated by the common use of fired heated reactors. Several studies have been undertaken to reduce the burden imposed by these (harsh) reaction conditions.

The study of Asensio J. M. et al., entitled "Hydrodeoxygenation using magnetic induction: high-temperature heterogeneous catalysis in solution" (Angew. Chem. Int. Ed., 2019, 58, 1-6) describes the use of magnetic nanoparticles as heating agents to improve the energy efficiency of reactions performed at high temperature, as the heat can be then directly and homogeneously transferred to the medium without the need for heating the reactor walls. This was applied in the hydrodeoxygenation of ketones. However, in such a system, relatively low temperatures up to 280° C. were reached and the reaction is exothermic.

In the study of Wismann S. T. et al., entitled "Electrified methane reforming: A compact approach to greener industrial hydrogen production" (Science, 2019, 364, 756-759), a conventional fired reactor was replaced by an electric-resistance-heated reactor. A laboratory-scale reactor based on FeCrAl alloy tube having a diameter of 6 mm and coated with a 130-μm nickel-impregnated washcoat was used to carry out steam methane reforming. As the heat source and the wall of the tube are one, it is possible to minimize the loss of heat and then to render more efficient and more economical the process of steam methane reforming. Temperatures with a maximum of 800° C. were reached with this kind of reactor.

In the study of Malerød-Fjeld H. et al., entitled "Thermo-electrochemical production of compressed hydrogen from methane with near-zero energy loss" (Nat. Energy, 2017, 2, 923-931), a ceramic tube, having an outer diameter of 1 cm and made of a perovskite derivative, is used as the electrolyte. By applying a voltage and hence a current across the electrolyte, hydrogen can be selectively extracted from methane and steam. The perovskite derivative is supplemented with nickel nanoparticles to provide the catalyst necessary for the reaction.

In the study of Varsano F. et al., entitled "Dry reforming of methane powered by magnetic induction" (Int. J. of Hydrogen Energy, 2019, 44, 21037-21044), electromagnetic induction heating of catalytic heterogeneous processes was used and has been demonstrated as bringing several advantages in terms of process intensification, energy efficiency, reactor setup simplification and safety issues coming from the use of radiofrequency. Temperatures ranging between 850° C. and 900° C. in reactors having 1 cm of inner diameter can be reached using $Ni_{60}Co_{60}$ pellets as heat mediators in a continuous-flow fixed-bed reactor.

These examples show that progress exists in the field of transforming fossils sources into valuable chemicals with the perspective to diminish the impact on the climate. However, this progress has not been developed to a large scale as it is rather limited to the laboratory environment.

With regards to this matter, the Shawinigan process, described in CA 573348, relates to a process to prepare hydrocyanic acid from ammonia using in a fluidized bed reactor made of high temperature-resistant silica glass and comprising conductive carbon particles, such as coke and/or petroleum coke. The principle resides in that the electricity is used to heat the conductive carbon particles which can maintain the fluidized bed at a temperature sufficient to transform ammonia into hydrocyanic acid, which is then recovered from the outgoing gas coming off the fluidized bed. The inner diameter of the reactor tube was 3.4 cm. A temperature ranging between 1300° C. and 1600° C., sufficient to perform the requested reaction, can be reached by using such conductive carbon particles.

U.S. Pat. No. 2,982,622 describes a method for producing hydrogen and high quality coke which comprises passing inert solid particles as a relatively dense mass downwardly through an elongated reaction zone, applying an electrical voltage of 0.1 to 1000 volts per inch across at least a portion of said solids mass in said reaction zone, said voltage being sufficient to raise the temperature of said solids to 1800 to 3000 F due to their resistance to the flow of electricity without causing substantial electrical spark discharges through said solids mass, downwardly withdrawing thus heated solids from said reaction zone, pre-heating a hydrocarbon feed by heat exchange with said withdrawn solids and introducing said preheated feed into and upwardly through said reaction zone in the form of an upwardly moving gasiform stream, said feed contacting said heated solids and being converted to light vapours including a substantial portion of hydrogen and carbon which deposits on said solids, heat exchanging hot vapours withdrawn from said reaction zone with inert solids in a heating zone, circulating at least a portion of the solids withdrawn from the reaction zone and previously heat exchanged with said feed to said heating zone, passing solids from said heating zone to said reaction zone as solids feed thereto, and recovering at least a portion of the solids withdrawn from the reaction zone as product and recovering hydrogen gas and light vapours from the upper portion of said reaction zone.

U.S. Pat. No. 3,259,565 describes a process for converting hydrocarbons to produce lower boiling hydrocarbons and solid coke particles of a size larger than fluidizable size which comprises passing coke agglomerates down through a hot fluidized bed of coke particles, introducing hydrocarbon oil feed into said fluidized bed to crack the hydrocarbon oil, passing cracked vaporous products overhead, removing coke agglomerates from said fluid bed and passing them down through a heat exchanger zone in counter-current contact with said withdrawn cracked vaporous products to cool said cracked vaporous products and to heat said coke agglomerates while condensing and depositing higher boiling hydrocarbons from said cracked vaporous products on said coke agglomerates, withdrawing resulting cracked vaporous products as product, recirculating the so treated coke agglomerates a number of times through said heat exchange zone to deposit hydrocarbons and through said hot fluidized coke bed to coke the deposited high boiling hydrocarbons and to increase the size of the coke agglomerates, withdrawing coke agglomerates of increased size as product from the system.

The disclosure of US 2017/0158516 described a fluidized-bed reactor made of silicon carbide for preparing granular polycrystalline silicon at the industrial level. The fluidized-bed reactor is heated using a heating device which is placed in an intermediate jacket between the outer wall of the reactor tube and the inner wall of the reactor vessel. Such intermediate jacket comprises an insulation material and is filled or flushed with an inert gas. It was found that the use of sintered silicon carbide (SSiC) having a SiC content of 98% by weight as the main element of the reactor tube with a high purity SiC coating deposited by chemical vapour deposition allowed reaching high temperature up to 1200° C. without the tube being corroded. It was also found that using siliconized silicon carbide (SiSiC) as the main element of the reactor tube without any surface treatment, such as the deposition of a coating layer, led to the tube being corroded.

On the other hand, the disclosure of Goldberger W. M. et al., entitled "*The electrothermal fluidized bed*" (*Chem. Eng. Progress*, 1965, 61 (2), 63-67, relates to fluidized-bed reactor made in graphite and susceptible to perform reactions such as the hydrocracking of hydrocarbons, the pyrolysis of organics, the production of elemental phosphorus or the chlorination of zirconium oxide. Operation at temperatures up to about 4400° C. appears possible. However, it is not certain that from the long-term perspective, the graphite material used to design the fluidized-bed reactor can resist such harsh reaction conditions. Indeed, in the study of Uda T. et al., entitled "*Experiments on high temperature graphite and steam reactions under loss of coolant accident conditions*", (*Fusion Engineering and Design*, 1995, 29, 238-246), it has been shown that graphite corrodes under conditions involving steam and elevated temperature, for instance between 1000° C. and 1600° C. Also, as shown in the study of Qiao M-X. et al., entitled "*Corrosion of graphite electrode in electrochemical advanced oxidation processes: degradation protocol and environmental application*", (*Chem. Eng. J.*, 2018, 344, 410-418), the graphite is susceptible to carbon oxidation reaction, which impacts its activity as an electrode by restricting notably the voltage that can be applied to it.

Direct conversion of methane into higher hydrocarbons is an endothermic process which typically produces large amounts of coke and acetylene if the process is non-catalytic due to lower stability of reaction products in comparison to methane:

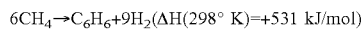
$$6CH_4 \rightarrow C_6H_6 + 9H_2 (\Delta H(298° K) = +531 \text{ kJ/mol})$$

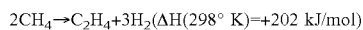
$$2CH_4 \rightarrow C_2H_4 + 3H_2 (\Delta H(298° K) = +202 \text{ kJ/mol})$$

Proper heat management is extremely important for the reaction to improve the selectivity to hydrocarbons. It could be achieved by using a fluidized bed that has already been exploited in disclosures, for instance, WO2007067285A1, however the heat for the reaction, in this case, is provided by fossil-derived energy. The heat was provided auto thermally from coke burning and injection of some additional hydrocarbon fuel. Alternatively, the same method of non-oxidative decomposition of methane could be used for complete non-catalytic pyrolysis of methane in the study of Simeiko K. V. entitled "Research thermal characteristics of the process of pyrolysis of methane in the electrothermal fluidized bed" (*Industrial Heat Engineering*, 2018, 40 (4), 83-90:

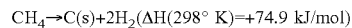
$$CH_4 \rightarrow C(s) + 2H_2 (\Delta H(298° K) = +74.9 \text{ kJ/mol})$$

The authors obtained a high level of conversion of methane but a negligible amount of hydrocarbons was formed. The majority of the carbon resulted in coke deposition.

The disclosure of U.S. Pat. No. 3,254,957 describes a process for cracking a hydrocarbon feed into coke using a fluidized bed reactor. The bed comprises coke particles. To heat the bed, the fluidized bed reactor is designed with an electrode zone and the application of a voltage allows to provide temperature ranging between 1900° F. (about 1000° C.) and 2800° F. (about 1500° C.).

The disclosure of CA 3 088 588 presents an electrically heatable packed pressure-bearing apparatus for conducting endothermic reactions, where at least a pair of electrodes are installed in the middle section of the apparatus in a vertical arrangement and where all the electrodes are disposed in an electrically conductive solid-state packing.

The present disclosure aims to provide a large-scale solution to one or more of the problems encountered in the prior art that is suitable for application in the industry, such as the chemical industry. The present disclosure aims to contribute to the replacement of the use of fossil carbon-based fuels heating devices in fluidized bed reactors by electricity. The present disclosure provides a solution to conduct endothermic catalytic methane pyrolysis to hydrocarbons and hydrogen.

SUMMARY

According to a first aspect, the disclosure provides for a process to perform an endothermic methane pyrolysis reaction, said process comprising the steps of:
a) providing at least one fluidized bed reactor comprising at least two electrodes, a bed comprising particles, and optionally a solid discharge system;
b) putting the particles of the bed in a fluidized state by passing upwardly through the said bed a fluid stream, to obtain a fluidized bed;
c) heating the fluidized bed to a temperature ranging from 500° C. to 1200° C. to conduct the endothermic methane pyrolysis reaction of a methane feedstock to produce a reactor effluent comprising at least solid carbon, hydrocarbons having at least two carbons and hydrogen;
d) optionally recovering from the reactor effluent produced at step (c) the hydrocarbons having at least two carbons and hydrogen;
the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 800° C. wherein the catalytic composition comprises one or more metallic compounds; in that the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof; and in that the step (c) of heating the fluidized bed is performed by passing an electric current through the fluidized bed.

For example, the fluid stream provided in step b) comprises a methane feedstock and optionally steam.

Surprisingly, it has been found that the use of electrically conductive particles such as silicon carbide, mixed oxides and/or mixed sulphides, said mixed oxides and/or said mixed sulphides being an ionic or mixed conductor, namely being doped with one or more lower-valent cations in one or more fluidized bed reactors which are electrified allows maintaining a temperature sufficient to carry out an endothermic pyrolysis reaction requesting high-temperature conditions such as temperature reaction ranging from 500° C. to 1200° C. without the need of any external heating device. The use of at least 10 wt. % of electrically conductive particles such as silicon carbide in the particles of the bed allows minimizing the loss of heat when a voltage is applied. Thanks to the Joule effect, most, if not all, the electrical energy is transformed into heat that is used for the heating of the reactor medium.

It is preferred that the at least one fluidized bed reactor comprising at least two electrodes and a bed comprising particles is devoid of packing.

The fluid stream may be a gaseous stream and/or a vaporized stream.

For example, the process further comprises a step (e) of recovering from the reactor effluent produced at step (c) the solid carbon. With preference, the process further comprises the step (f) of transforming said solid carbon into graphite. With preference, the step (f) of transforming said solid carbon into graphite comprises heating the solid carbon to a temperature ranging from 2000° C. to 4000° C.; preferably from 2500° C. to 3500° C.

For example, the process further comprises the step (g) of fractionating at least a part of the hydrocarbons having at least two carbons and hydrogen recovered at step (d), to generate acetylene, ethylene, paraffins, aromatics, and/or hydrogen.

For example, the reactor effluent produced at step (c) further comprises unreacted methane, and the process further comprises the step (h) of recycling at least a part of the hydrocarbons having at least two carbons and/or said unreacted methane in step (c).

In a preferred embodiment, the volumetric heat generation rate is greater than 0.1 $MW/m^3$ of fluidized bed, more preferably greater than 1 $MW/m^3$, in particular, greater than 3 $MW/m^3$.

In a preferred embodiment, the at least one fluidized bed reactor is devoid of heating means; for example, the at least one fluidized bed reactor is devoid of heating means located around or inside the vessel.

The solid particulate material (i.e. the particles) used in the fluidized bed reactor consists of solid particles having electrical conductivity allowing generating heat and a catalytic particulate material to catalyse the pyrolysis reaction. The catalytic particulate material can also be electrically conductive and hence contribute to the generation of heat for the endothermal reaction.

The present disclosure provides, therefore, a solution to conduct an endothermic reactor in a "cold wall" type of reactor", where the energy is supplied directly to the catalyst (not from the reactor walls creating a huge radial temperature gradient).

The Electrically Conductive Particles of the Bed

For example, the content of electrically conductive particles based on the total weight of the bed is ranging from 10 wt. % to 100 wt. %; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the content of electrically conductive particles based on the total weight of the bed is ranging from 10 wt. % to 100 wt. %; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles have a resistivity ranging from 0.005 to 400 Ohm·cm at 800° C., preferably ranging from 0.01 to 300 Ohm·cm at 800° C.; more preferably ranging from 0.05 to 150 Ohm·cm at 800° C. and most preferably ranging from 0.1 to 100 Ohm·cm at 800° C.

For example, the electrically conductive particles have a resistivity of at least 0.005 Ohm·cm at 800° C.; preferably of at least 0.01 Ohm·cm at 800° C., more preferably of at least 0.05 Ohm·cm at 800° C.; even more preferably of at least 0.1 Ohm·cm at 800° C., and most preferably of at least 0.5 Ohm·cm at 800° C.

For example, the electrically conductive particles have a resistivity of at most 400 Ohm·cm at 800° C.; preferably of at most 300 Ohm·cm at 800° C., more preferably of at most 200 Ohm·cm at 800° C.; even more preferably of at most 150 Ohm·cm at 800° C., and most preferably of at most 100 Ohm·cm at 800° C.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

The selection of the content of electrically conductive particles based on the total weight of the bed and of the electrically conductive particles of a given resistivity influence the temperature reached by the fluidized bed. Thus, in case the targeted temperature is not attained, the person skilled in the art may increase the density of the bed of particles, the content of electrically conductive particles based on the total weight of the bed and/or select electrically conductive particles with a lower resistivity to increase the temperature reach by the fluidized bed.

For example, the density of the bed of particles is expressed as the void fraction. Void fraction or bed porosity is the volume of voids between the particles divided by the total volume of the bed. At the incipient fluidisation velocity, the void fraction is typically between 0.4 and 0.5. The void fraction can increase up to 0.98 in fast fluidised beds with lower values at the bottom of about 0.5 and higher than 0.9 at the top of the bed. The void fraction can be controlled by the linear velocity of the fluidising gas and can be decreased by recycling solid particles that are recovered at the top and send back to the bottom of the fluidized bed, which compensates for the entrainment of solid particles out of the bed.

The void fraction VF is defined as the volume fraction of voids in a bed of particles and is determined according to the following equation:

$$VF = \frac{Vt - Vp}{Vt} \qquad (1)$$

wherein Vt is the total volume of the bed and is determined by $$Vt = AH \qquad (2)$$

wherein A is the cross-sectional area of the fluidized bed and H is the height of the fluidized bed; and wherein Vp is the total volume of particles within the fluidized bed.

For example, the void fraction of the bed is ranging from 0.5 to 0.8; preferably ranging from 0.5 to 0.7, more preferably from 0.5 to 0.6. To increase the density of the bed of particles, the void fraction is to be reduced.

For example, the electrically conductive particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the electrically conductive particles of the bed are or comprise one or more particles selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations and/or one or more and/or mixed sulphides being doped with one or more lower-valent cations and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed comprise graphite and one or more selected from carbon black, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations and/or one or more mixed sulphides being doped with one or more lower-valent cations and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

As an alternative, the electrically conductive particles of the bed are or comprise one or more particles selected from one or more metallic alloys, one or more non-metallic resistors, provided that the non-metallic resistor is not silicon carbide, one or more metallic carbides, one or more transition metal nitrides, one or more metallic phosphides, graphite, carbon black, one or more superionic conductors, one or more phosphate electrolytes, one or more mixed oxides being doped with one or more lower-valent cations and/or one or more and/or mixed sulphides being doped with one or more lower-valent cations and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more non-metallic resistors, graphite, carbon black, one or more superionic conductors, one or more phosphate electrolytes, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, said one or more metallic alloys particles are selected from Ni—Cr, Fe—Ni—Cr, Fe—Ni—Al or a mixture thereof. With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

For example, non-metallic resistors particles are selected from silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof; preferably non-metallic resistors particles are silicon carbide. However, in an alternative embodiment, the non-metallic resistors are devoid of silicon carbide. In said alternative embodiment, said non-metallic resistors particles are selected from molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof.

For example, said one or more metallic carbides are selected from iron carbide ($Fe_3C$), molybdenum carbide (such as a mixture of MoC and $Mo_2C$).

For example, said one or more transition metal nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN).

For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

For example, said one or more mixed oxides are ionic or mixed conductors being doped with one or more lower-valent cations. Advantageously, said mixed oxides are doped with one or more lower-valent cations, and are respectively selected from oxides having a cubic fluorite structure, perovskite, and/or pyrochlore.

For example, said one or more mixed sulphides are ionic or mixed conductors being doped with one or more lower-valent cations.

For example, the electrically conductive particles of the bed are or comprise silicon carbide. For example, the silicon carbide is selected from sintered silicon carbide, nitride-bounded silicon carbide, recrystallised silicon carbide, reaction bonded silicon carbide and any mixture thereof. The type of silicon carbide material is selected according to the required heating power necessary for supplying the reaction heat of methane pyrolysis.

For example, the electrically conductive particles of the bed are or comprise a mixture of a non-metallic resistor being silicon carbide and electrically conductive particles different from said silicon carbide. The presence of electrically conductive particles different from said silicon carbide in the bed is optional. It can be present as a starting material for heating the bed since it was found that the resistivity of silicon carbide at room temperature is too high to start heating the bed. Alternatively to the presence of electrically conductive particles different from silicon carbide, it is possible to provide heat to the reactor for a defined time to start the reaction.

For example, the electrically conductive particles of the bed are or comprise a mixture of a non-metallic resistor being silicon carbide and electrically conductive particles different from said silicon carbide and the electrically conductive particles of the bed comprises from 10 wt. % to 99 wt. % of silicon carbide based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of a non-metallic resistor being silicon carbide and electrically conductive particles different from said silicon carbide and the electrically conductive particles different from silicon carbide are graphite particles and/or one or more mixed oxides being doped with one or more lower-valent cations, and/or one more mixed sulphides being doped with one or more lower-valent cations.

For example, the electrically conductive particles of the bed are or comprise one or more mixed oxides being ionic conductor, namely being doped with one or more lower-valent cations; with preference, the mixed oxides being doped with one or more lower-valent cations are selected from:
- one or more oxides having a cubic fluorite structure being at least partially substituted with one or more lower-valent cations; preferably selected from Sm, Gd, Y, Sc, Yb, Mg, Ca, La, Dy, Er, Eu; and/or
- one or more $ABO_3$-perovskites with A and B tri-valent cations being at least partially substituted in A position with one or more lower-valent cations, preferably selected from Ca, Sr, or Mg, and comprising at least one of Ni, Ga, Co, Cr, Mn, Sc, Fe and/or a mixture thereof in B position; and/or
- one or more $ABO_3$-perovskites with A bi-valent cation and B tetra-valent cation, being at least partially substituted with one or more lower-valent cations, preferably selected from Mg, Sc, Y, Nd or Yb in the B position or with a mixture of different B elements in the B position; and/or
- one or more $A_2B_2O_7$-pyrochlores with A tri-valent cation and B tetra-valent cation, being at least partially substituted in A position with one or more lower-valent cations, preferably selected from Ca or Mg, and comprising at least one of Sn, Zr and Ti in B position.

Examples of one or more mixed sulphides are
- one or more sulphides having a cubic fluorite structure being at least partially substituted with one or more lower-valent cations; preferably selected from Sm, Gd, Y, Sc, Yb, Mg, Ca, La, Dy, Er, Eu; and/or
- one or more $ABS_3$ structures with A and B tri-valent cations being at least partially substituted in A position with one or more lower-valent cations, preferably selected from Ca, Sr, or Mg, and comprising at least one of Ni, Ga, Co, Cr, Mn, Sc, Fe and/or a mixture thereof in B position; and/or
- one or more $ABS_3$ structures with A bi-valent cation and B tetra-valent cation, being at least partially substituted with one or more lower-valent cations, preferably selected from Mg, Sc, Y, Nd or Yb in the B position or with a mixture of different B elements in the B position; and/or
- one or more $A_2B_2S_7$ structures with A tri-valent cation and B tetra-valent cation, being at least partially substituted in A position with one or more lower-valent cations, preferably selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed sulphide doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B2S_7$ structures with A trivalent cation and B tetra-valent cation respectively, preferably between 3 and 20 atom %, more preferably between 5 and 15 atom %.

For example, the electrically conductive particles of the bed comprise one or more metallic alloys; with preference, one or more metallic alloys are selected from Ni—Cr, Fe—Ni—Cr, Fe—Ni—Al or a mixture thereof.

With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

In the case where said electrically conductive particles different from said silicon carbide particles are particles are selected from non-metallic resistors, said non-metallic resistor is preferably molybdenum disilicide ($MoSi_2$).

For example, the electrically conductive particles of the bed are or comprise graphite and/or carbon black. Alternatively, the electrically conductive particles of the bed are devoid of graphite and/or carbon black For example, the electrically conductive particles of the bed comprise a mixture of silicon carbide particles and electrically conductive particles different from said silicon carbide wherein the electrically conductive particles different from said silicon carbide particles is or comprises graphite particles and one or more wherein the graphite particles have an average particle size ranging from 5 to 300 μm as determined by sieving according to ASTM D4513-11, more preferably ranging from 10 to 200 μm and most preferably ranging from 30 to 150 μm.

The Particles of a Catalytic Composition

For example, the content of the particles of a catalytic composition based on the total weight of the particle of the bed is ranging from 10 wt. % to 100 wt. %; preferably from 15 wt. % to 99 wt. %, more preferably from 20 wt. % to 95 wt. %, more preferably from 35 wt. % to 90 wt. %, even more preferably from 40 wt. % to 85 wt. %, most preferably from 45 wt. % to 80 wt. % and even most preferably from 50 wt. % to 75 wt. %. In the case where the content of the particles of a catalytic composition based on the total weight of the particles of the bed is 100 wt. %, said particles of a catalytic composition are also electrically conductive particles.

For example, the particles of a catalytic composition have an average particle size ranging from 5 to 300 μm as determined by sieving according to ASTM D4513-11, preferably ranging from 10 to 200 μm and more preferably ranging from 20 to 200 μm or from 30 to 150 μm.

In an embodiment, the catalytic composition comprises one or more metallic compounds selected from Ca, Mg, Ba, Y, La, Sc, Ce, Ti, Zr, Hf, V, Nb, Ta, Cr, Mo, W, Mn, Re, Fe, Ru, Co, Rh, Ir, Ni, Pd, Cu, Ag, Au, Zn, Al, Ga, Si, Ge, In, Sn, Pb, or Bi; preferably one or more metallic compounds selected from Fe, Mo, W or Re; more preferably the one or more metallic compounds are selected from Fe, Mo and W; even more preferably the one or more metallic compounds are selected from Mo and/or W, and most preferably the metallic compound is Mo. These metallic compounds can be under a metallic form (i.e. the elemental form) and/or under one or more forms selected from a metal oxide, carbide, sulphide, nitride or phosphide form. These metallic elements can be supported or not.

Optionally, the catalytic composition comprises boron.

The Catalytic Support of the Catalytic Composition

With preference, one or more metallic compounds are deposited on a catalyst support in an amount ranging from 0.1 wt. % to 20.0 wt. % based on the total weight of said catalyst composition, preferably from 0.5 wt. % to 15.0 wt. %, more preferably from 1.0 to 10.0 wt. %, even more preferably from 1.5 to 5.0 wt. %.

With preference, the catalytic composition comprises a catalytic support, preferably in a content of at least 60 wt. % based on the total molar content of the catalyst composition, more preferably at least 70 wt. %, even more preferably at least 80 wt. %, most preferably at least 90 wt. %. When the catalyst composition comprises a catalytic support, said catalytic support is preferably selected from oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements; more preferably said catalytic support is $Al_2O_3$. Alternatively, or also, the catalyst support is one or more porous materials, one or more carbon materials (such as carbon black, activated carbon, graphite, carbon fibers, biochar, carbon nanotubes, carbon xerogels, graphene), one or more microporous crystalline materials like one or more zeolites or a mesoporous material.

For example, the catalyst composition comprises one or more zeolites, preferably in a content of at least 60 wt. % based on the total molar content of the catalyst composition, more preferably at least 70 wt. %, even more preferably at least 80 wt. %, most preferably at least 90 wt. %. Then, the following features further define said one or more zeolites:

- The one or more zeolites have a crystalline aluminosilicate oxide framework substituted with a metal, said metal being preferably selected from Fe, Sn, Hf, Zn, Zr, Ti, V, Ta, Ga, Ge, Nb, Mn, Mo, W, Co, and/or Cd.
- The one or more zeolites have a crystalline aluminosilicate oxide framework substituted with phosphorus.
- The one or more zeolites have a crystalline aluminosilicate oxide framework comprising tin, molybdenum, tungsten, and/or iron in the tetrahedral sites of the framework.
- The one or more zeolites comprise a molar ratio of silicon over the sum between the amount of the aluminium and the metallic element (i.e. a Si/(Al+M) (M=metal) molar ratio) of at least 5, preferably of at least 10, more preferably of at least 20.
- The one or more zeolites comprise a molar ratio of silicon over the sum between the amount of the aluminium and the metallic element (i.e. a Si/(Al+M) (M=metal) molar ratio) ranging between 5 and 1000, preferably between 10 and 900, more preferably between 20 and 800, even more preferably between 50 and 700, most preferably between 100 and 600.
- The one or more zeolites have a crystalline aluminosilicate oxide framework with an anionic charge which is advantageously balanced by cationic elements selected from H, Li, Na, K, Cs, Mg, Ca, Sr, Ba, La and/or Ce.
- The one or more zeolites are in a sodium form, in a protonic form or in a protonic/sodium form. Advantageously, the one or more zeolites are modified by ion-exchange or impregnated with one or more alkali metal cations, such as Li, K, and/or Cs; and/or with one or more alkali-earth metal cations, such as Mg, Ca, Sr, or Ba; and/or with one or more transition metal cations, such as Fe, Ni, Cu, Mn, V, W; and/or with one or more rare-earth metal cations, such as La or Ce. Such subsequent ion-exchange or impregnation may replace the charge-balancing counter-ions, but furthermore may also partially replace ions in the oxide framework resulting in a modification of the crystalline make-up and structure of the oxide framework.

The one or more zeolites are synthesized without an organic template.

The one or more zeolites are subjected to a step of steaming before step (c) of the process. With preference, the step of steaming is conducted at a temperature ranging between 400° C. and 1000° C., more preferably between 450° C. and 950° C., even more preferably between 500° C. and 900° C.; and/or at a pressure of 0.01 MPa or more.

For example, the one or more zeolites are selected from the list comprising AEL, AFI, AFO, BEA, CHA, ERI, FAU, FER, ITE, ITH, IWR, IWS, IWW, KFI, LEV, LTL, MEL, MFI, MFS, MOR, MSE, MTT, MTW, MWW, TON and/or VFI families. With preference, the zeolite is a zeolite from the MFI family.

When the zeolite is selected from the AEL family, the zeolite is or comprises SAPO-11.

When the zeolite is selected from the AFI family, the zeolite is or comprises ALPO-5.

When the zeolite is selected from the AFO family, the zeolite is or comprises SAPO-41.

When the zeolite is selected from the BEA family, the zeolite is or comprises zeolite beta.

When the zeolite is selected from the CHA family, the zeolite is or comprises SAPO-34.

When the zeolite is selected from the ERI family, the zeolite is or comprises SAPO-17.

When the one or more zeolites are selected from the FAU family, the one or more zeolites are preferably one or more selected from zeolite X, zeolite Y, ultrastabilized zeolite Y and dealuminized zeolite Y.

When the zeolite is selected from the FER family, the zeolite is or comprises ZSM-35.

When the zeolite is selected from the ITE family, the zeolite is or comprises ITQ-3.

When the zeolite is selected from the ITH family, the zeolite is or comprises ITQ-13.

When the zeolite is selected from the IWR family, the zeolite is or comprises ITQ-24.

When the zeolite is selected from the IWR family, the zeolite is or comprises ITQ-26.

When the zeolite is selected from the IWW family, the zeolite is or comprises ITQ-22.

When the zeolite is selected from the KFI family, the zeolite is or comprises ZK-5.

When the zeolite is selected from the LEV family, the zeolite is or comprises SAPO-35.

When the zeolite is selected from the LTL family, the zeolite is or comprises zeolite L.

When the zeolite is selected from the MEL family, the zeolite is or comprises ZSM-11.

When the one or more zeolites are selected from the MFI family, the one or more zeolites are preferably one or more selected from ZSM-5, TS-1, TS-2 and silicalite, more preferably the zeolite is ZSM-5.

When the zeolite is selected from the MFS family, the zeolite is or comprises ZSM-57.

When the zeolite is selected from the MOR family, the zeolite is or comprises mordenite.

When the zeolite is selected from the MSE family, the zeolite is or comprises MCM-68.

When the zeolite is selected from the MTT family, the zeolite is or comprises ZSM-23.

When the zeolite is selected from the MTW family, the zeolite is or comprises ZSM-12.

When the one or more zeolites are selected from the MWW family, the one or more zeolites are preferably one or more selected from MCM-22, PSH-3, SSZ-25, ERB-I, ITQ-I, ITQ-2, MCM-36, MCM-49 and MCM-56.

When the zeolite is selected from the TON family, the zeolite is or comprises ZSM-22.

When the zeolite is selected from the VFI family, the zeolite is or comprises VPI-5.

With preference, when the catalytic support is one or more zeolites, the catalyst composition further comprises a binder, preferably in a content ranging between 5 wt. % and 80 wt. % based on the total molar content of the catalyst composition, more preferably ranging between 10 wt. % and 70 wt. %, even more preferably ranging between 15 wt. % and 60 wt. %, most preferably between 20 wt. % and 50 wt. %, even most preferably between 25 wt. % and 40 wt. %. In this case, the binder is advantageously selected from silica, alpha-alumina, clays, alumina phosphates, calcium phosphates, magnesium phosphates, mullite, or a mixture thereof; preferably the binder is silica.

For example, the catalyst composition comprises one or more mesoporous materials, preferably in a content of at least 60 wt. % based on the total molar content of the catalyst composition, more preferably at least 70 wt. %, even more preferably at least 80 wt. %, most preferably at least 90 wt. %. In this case, the one or more mesoporous materials are advantageously selected from MCM-41, MCM-48, MCM-50, FSM-16 and/or SBA-15.

The Endothermic Pyrolysis of Methane

For example, said pyrolysis reaction is conducted at a temperature ranging from 550° C. to 1200° C., preferably from 600° C. to 1150° C., and most preferably from 700° C. to 1100° C.

For example, said pyrolysis reaction is performed at a pressure ranging between 0.1 MPa and 10 MPa, preferably between 0.5 MPa and 5 MPa.

For example, said at least two electrodes are made in carbon, stainless steel material or nickel-chromium alloys; or nickel-chromium-iron alloys.

In an embodiment, said process comprises a step of pre-heating with a gaseous stream said fluidized bed reactor before conducting said endothermic reaction in the fluidized bed reactor; with preference, said gaseous stream is a stream of inert gas and/or has a temperature comprised between 500° C. and 1200° C. The said embodiment is of interest when the electrically conductive particles of the bed have too high resistivity at room temperature to start the electro-heating of the bed.

For example, said endothermic pyrolysis is performed at a weight hourly space velocity (defined as the ratio of mass flow of reaction stream to the mass of solid particulate material in the fluidized bed) of said reaction stream comprised between 0.1 $h^{-1}$ and 100 $h^{-1}$, preferably comprised between 1.0 $h^{-1}$ and 50 $h^{-1}$, more preferably comprised between 1.5 $h^{-1}$ and 10 $h^{-1}$, even more preferably comprised between 2.0 $h^{-1}$ and 6.0 $h^{-1}$. The weight hourly space velocity is defined as the ratio of mass flow of the reaction stream to the mass of solid particulate material in the fluidized bed.

For example, the said at least two electrodes are made in electrically conductive material; with preference, said at least two electrodes are made in graphite or stainless-steel material or nickel-chromium alloys; or nickel-chromium-iron alloys.

In a preferred embodiment, the outlet temperature of the reactor may range from 800 to 1200° C., preferably from 820 to 1100° C., more preferably from 830 to 950° C., more preferably from 840° C. to 900° C.

For example, the fluid stream provided in step (b) is a gaseous fluid stream. The fluid stream may be a vaporized stream.

For example, the step of heating the fluidized bed is performed by passing an electric current of at most 300 V through the fluidized bed, preferably at most 200 V, more preferably at most 150 V, even more preferably at most 120 V, most preferably at most 100 V, even most preferably at most 90 V.

The Installation

According to a second aspect, the disclosure provides an installation to perform an endothermic methane pyrolysis reaction according to the first aspect, said installation comprises at least one fluidized bed reactor comprising:
- at least two electrodes, with preference, one electrode is a submerged central electrode or two electrodes are submerged electrodes,
- optionally, a solid discharge system,
- a reactor vessel;
- one or more fluid nozzles for the introduction of a fluidizing gas and/or of a methane feedstock within the reactor; and
- a bed comprising particles;

the installation is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 800° C.; wherein the catalytic composition comprises one or more metallic compounds and wherein the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof.

The particles of a catalytic composition could be electrically conductive or not.

Advantageously, the fluidized bed reactor is devoid of heating means. For example, the fluidized bed reactor is devoid of heating means located around or inside the reactor vessel.

For example, all the fluidized bed reactors are devoid of heating means. When stating that at least one of the fluidized bed reactor is devoid of "heating means", it refers to "classical" heating means, such as ovens, gas burners, hot plates and the like. There are no other heating means than the at least two electrodes of the fluidized bed reactor itself. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

For example, the fluidizing gas is one or more diluent gases.

For example, the at least one reactor vessel has an inner diameter of at least 100 cm, preferably at least 200 cm, more preferably at least 300 cm.

With preference, the reactor vessel comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ).

With preference, one of the electrodes is the reactor tube or the gas distributor and/or said at least two electrodes are made in stainless steel material or nickel-chromium alloys or nickel-chromium-iron alloys.

For example, the at least one fluidized bed reactor comprises a heating zone and a reaction zone, one or more fluid nozzles to provide a methane feedstock to the reaction zone, and optional means to transport the particles of the bed from the reaction zone back to the heating zone.

For example, the installation comprises at least two fluidized bed reactors connected one to each other wherein at least one reactor of said at least two fluidized bed reactors is the heating zone and at least another reactor of said at least two fluidized bed reactors is the reaction zone. With preference, the installation comprises one or more fluid nozzles arranged to inject a methane feedstock to the at least one fluidized bed reactor being the reaction zone, means to transport the particles of the bed from the heating zone to the reaction zone when necessary and optional means to transport particles from the reaction zone back to the heating zone. This configuration is remarkable in that a given particle bed is common to at least two fluidized bed reactors.

For example, the at least one fluidized bed reactor is a single one fluidized bed reactor wherein the heating zone is the bottom part of the fluidized bed reactor while the reaction zone is the top part of the fluidised bed reactor. With preference, the installation comprises one or more fluid nozzles to inject a methane feedstock between the two zones. The diameter of the heating zone and reaction zone can be different to accomplish optimum conditions for heating in the bottom zone and optimum conditions for methane conversion in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone.

For example, the at least one fluidized bed comprises at least two lateral zones being an outer zone and an inner zone wherein the outer zone is surrounding the inner zone, with the outer zone being the heating zone and the inner zone being the reaction zone. In a less preferred configuration, the outer zone is the reaction zone and the inner zone is the heating zone. With preference, the installation comprises one or more fluid nozzles to inject a hydrocarbon feedstock in the reaction zone.

For example, the at least one fluidized bed reactor is devoid of packing.

The Use of a Particle Bed

According to a third aspect, the disclosure provides the use of a particle bed in a fluidized bed reactor to perform a process of endothermic methane pyrolysis according to the first aspect, the use is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 800° C., wherein the catalytic composition comprises one or more metallic compounds and wherein the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof.

For example, the at least one fluidized bed reactor is devoid of packing.

For example, the use comprises heating the bed comprising particles to a temperature ranging from 500° C. to 1200° C. in a first reactor, transporting the heated particle bed from the first reactor to a second reactor and providing a methane feedstock to the second reactor; with preference, at least the second reactor is a fluidized bed reactor and/or at least the second reactor is devoid of heating means; more preferably, the first reactor and the second reactor are fluidized bed reactors and/or the first and the second reactor are devoid of heating means. For example, the second reactor is devoid of electrodes.

For example, at least the second reactor is devoid of heating means selected from ovens, gas burners, hot plates, or any combination thereof. For example, the first and the second reactors are devoid of heating means selected from ovens, gas burners, hot plates, or any combination thereof.

The Use of the Installation

According to a fourth aspect, the disclosure provides the use of an installation comprising at least one fluidized bed reactor to perform an endothermic methane pyrolysis reaction, remarkable in that the installation is according to the second aspect. With preference, the use of an installation at least one fluidized bed reactor to perform an endothermic methane pyrolysis reaction in a process according to the first aspect.

For example, the at least one fluidized bed reactor comprising at least two electrodes and a bed comprising particles is devoid of packing.

The particular features, structures, characteristics or embodiments may be combined in any suitable manner, as would be apparent to a person skilled in the art from this disclosure, in one or more embodiments.

TABLE 1

| Sample | Mo-MFI | SiMFI |
|---|---|---|
| Space group | P21/n (monoclinic) | Pnma (orthorhombic) |
| a | 19.8876(6) | 19.8868(6) |
| b | 20.1177(4) | 20.0577(5) |
| c | 13.3858(9) | 13.3701(5) |
| α | 90 | 90 |
| β | 90.5491(3) | 90 |
| γ | 90 | 90 |
| Volume (Å$^3$) | 5355.37(9) | 5333.13(0) |
| GOF$^a$ | 1.42 | 1.36 |
| Rp$^b$ | 2.74 | 3.85 |
| wRp$^c$ | 3.57 | 5.08 |

$^a$Goodness of fit
$^b$Expected R-factor
$^c$Weight Profile R-factor

Table 1 showing the Le Bail profile refinement results (unit cell parameters, and refinement values) for MoMFI and SiMFI examples. Samples used for Le Bail refinement were recorded from 3 to 80° 2θ for 10h.

Figure 8:
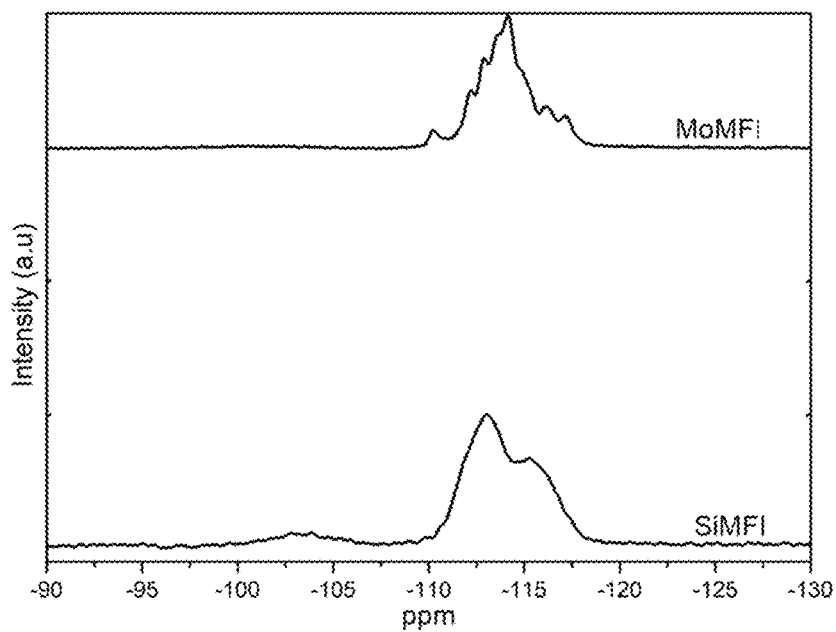

FIG. 8 shows $^{29}$Si solid-state Magic Angle Spinning Nuclear Magnetic Resonance (MAS NMR) spectra of MoMFI and SiMFI samples obtained after the calcination step (h). The absence of Q3 species and high resolution of Q4 species was obtained indicating the very low amount of silanol defects in the metal-containing samples, and the local homogeneity of the samples, with regards to purely siliceous MFI zeolite (sample SiMFI).

Figure 9:
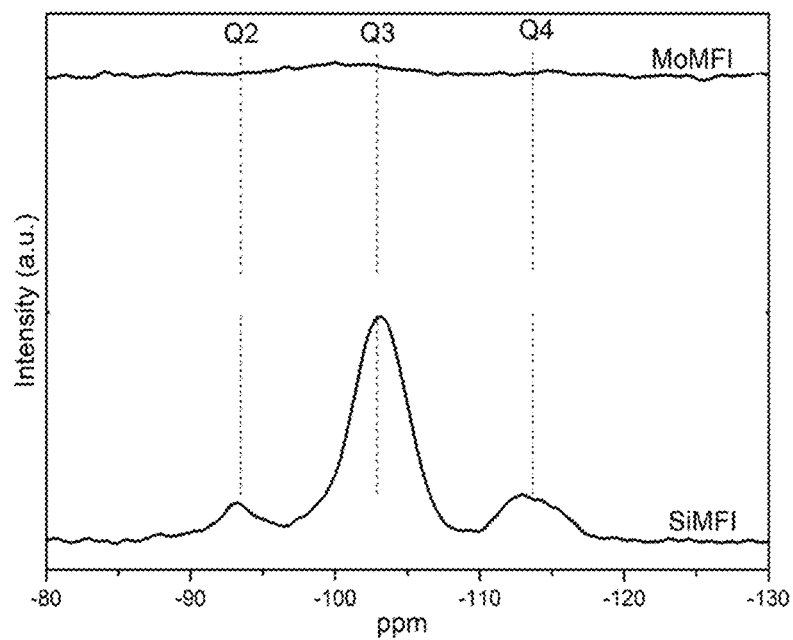

FIG. 9 represents the {$^1$H} $^{29}$Si solid-state Cross Polarization Magic Angle Spinning Nuclear Magnetic Resonance (CP MAS NMR) experiment for sample MoMFI and SiMFI, where the absence/negligible amount of silanols is demonstrated through the absence of any signal for both metal-containing samples with regards to sample SiMFI.

Figure 10:
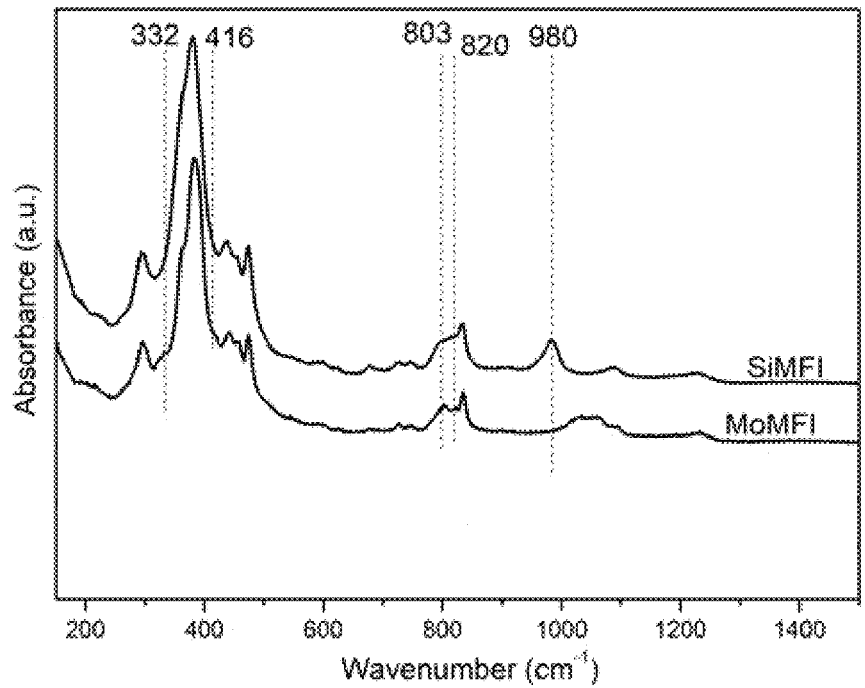

FIG. 10 represents the Raman spectra of samples SiMFI and MoMFI. The absence of any metal oxide phase is confirmed for all samples. New contributions at 332, 416, 803, and 820 cm$^{-1}$ indicate the presence of framework metal species. The low amount of silanol defects can also be observed by the absence of a signal at about 980 cm$^{-1}$ for metal-containing zeolites. No peaks corresponding to the oxide phase of molybdenum (higher intensity band expected at 980 cm$^{-1}$) or tin (higher intensity band expected at 632 cm$^{-1}$) can be observed, indicating the absence of oxide species in both samples.

Figure 11:
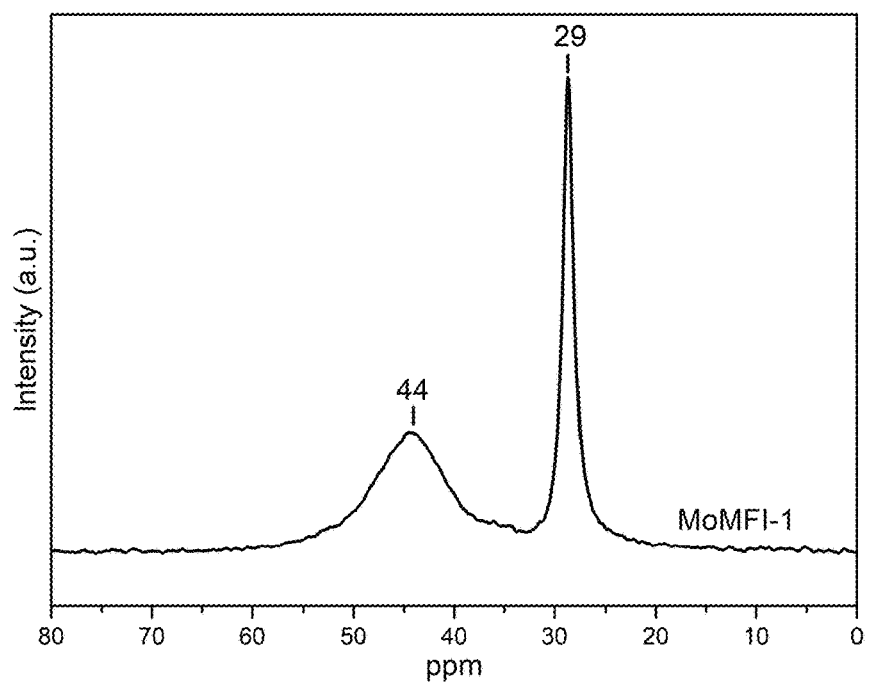

FIG. 11 presents the $^{31}$P solid-state MAS NMR spectra of TMPO interacting with MoMFI sample. Two peaks can be observed at 29 and 44 ppm, corresponding to respectively:

physisorbed TMPO and TMPO interacting with Lewis acid sites from the MFI zeolite, which are actual Mo framework sites.

Figure 12:
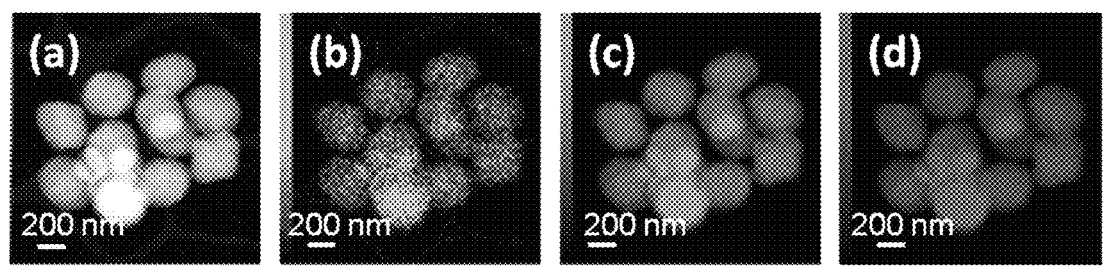

FIG. 12 presents the Scanning Transmission Electron Microscope-Energy Dispersive X-Ray Spectroscopy (STEM-EDS) micrographs (a) of sample MoMFI. The homogeneous distribution (b) of Mo, (c) of Si and (d) of O in the MFI framework are shown.

Figure 13:
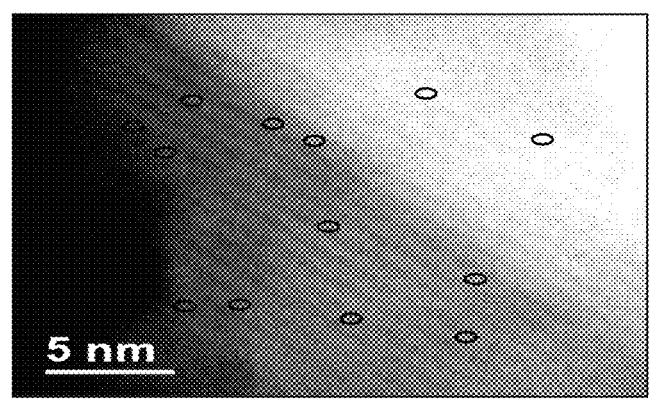

FIG. 13 shows a high-resolution High-Angle Annular Dark Field-Scanning Transmission Electron Microscope (HAADF-STEM) image of sample MoMFI. The Z-sensitive contrast obtained using this imaging technique allows observing the presence of the Mo metal sites in the structure. Mo appears as white dots. Due to the location and size of these sites, it can be concluded that Mo atoms are atomically dispersed in the zeolite MFI framework.

DETAILED DESCRIPTION

For the disclosure, the following definitions are given:

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

Zeolite codes (e.g., CHA . . . ) are defined according to the "*Atlas of Zeolite Framework Types*", 6$^{th}$ revised edition, 2007, Elsevier, to which the present application also refers.

The present disclosure provides for a process to perform endothermic methane pyrolysis, said process comprising the steps of:
a) providing at least one fluidized bed reactor comprising at least two electrodes, a bed comprising particles, and optionally a solid discharge system;
b) putting the particles of the bed in a fluidized state by passing upwardly through the said bed a fluid stream, to obtain a fluidized bed;
c) heating the fluidized bed to a temperature ranging from 500° C. to 1200° C. to conduct the endothermic methane pyrolysis reaction to produce a reactor effluent comprising at least solid carbon, hydrocarbons having at least two carbons and hydrogen;
d) optionally recovering from the reactor effluent produced at step (c) the hydrocarbons having at least two carbons and hydrogen;

the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 800° C., wherein the catalytic composition comprises one or more metallic compounds, in that the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof; and in that the step (c) of heating the fluidized bed is performed by passing an electric current through the fluidized bed.

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

For example, the process further comprises a step (e) of recovering from the reactor effluent produced at step (c) the solid carbon. With preference, the process further comprises the step (f) of transforming said solid carbon into graphite. With preference, the step (f) of transforming said solid carbon into graphite comprises heating the solid carbon to a temperature ranging from 2000° C. to 4000° C.; preferably from 2500° C. to 3500° C.

For example, the process further comprises the step (g) of fractionating at least a part of the hydrocarbons having at least two carbons and hydrogen recovered at step (d), to generate acetylene, ethylene, paraffins, aromatics, and/or hydrogen.

For example, the reactor effluent produced at step (c) further comprises unreacted methane, and the process further comprises the step (h) of recycling at least a part of the hydrocarbons having at least two carbons and/or said unreacted methane in step (c).

The solid particulate material (i.e. the particles) in the fluidized bed reactor is typically supported by a porous plate, a perforated plate, a plate with nozzles or chimneys, known as a distributor. The fluid is then forced through the distributor up and travelling through the voids between the solid particulate material. At lower fluid velocities, the solids remain settled as the fluid passes through the voids in the material, known as a packed bed reactor. As the fluid velocity is increased, the particulate solids will reach a stage where the force of the fluid on the solids is enough to counterbalance the weight of the solid particulate material. This stage is known as incipient fluidization and occurs at this minimum fluidization velocity. Once this minimum velocity is surpassed, the contents of the reactor bed begin to expand and become fluidized. Depending on the operating conditions and properties of the solid phase various flow regimes can be observed in such reactors. The minimum fluidization velocity needed to achieve bed expansion depends upon the size, shape, porosity and density of the particles and the density and viscosity of the upflowing fluid.

P. R. Gunjal, V. V. Ranade, in Industrial Catalytic Processes for Fine and Specialty Chemicals, (2016) reads that four different categories of fluidization based on the mean particle have been differentiated by Geldart that determine the fluidization regimes:
  type A, aeratable fluidization (medium size, medium-density particles which are easier to fluidize; Particles of typically 30-100 μm, density ~1500 kg/m$^3$);
  type B, sand-like fluidization (heavier particles which are difficult to fluidize; Particles of typically 100-800 μm, density between 1500 and 4000 kg/m$^3$);
  type C, cohesive fluidization (typical powder-like solid particle fluidization; Fine-size particles (~20 μm) with a dominance of intraparticle or cohesive forces); and type D, spoutable fluidization (large density and larger particle ~1-4 mm, dense and spoutable).

Fluidization may be broadly classified into two regimes (Fluid Bed Technology in Materials Processing, 1999 by CRC Press): homogeneous fluidization and heterogeneous fluidization. In homogeneous or particulate fluidization, particles are fluidized uniformly without any distinct voids. In heterogeneous or bubbling fluidization, gas bubbles devoid of solids are distinctly observable. These voids behave like bubbles in gas-liquid flows and exchange gas with the surrounding homogeneous medium with a change in size and shape while rising in the medium. In particulate fluidization, the bed expands smoothly with substantial particle movement and the bed surface is well defined. Particulate fluidization is observed only for Geldart-A type particles. A bubbling fluidization regime is observed at much higher velocities than homogeneous fluidization, in which distinguishable gas bubbles grow from the distributor, may coalesce with other bubbles and eventually burst at the surface of the bed. These bubbles intensify the mixing of solids and gases and bubble sizes tend to increase further with a rise in fluidization velocity. A slugging regime is observed when the bubble diameter increases up to the reactor diameter. In a turbulent regime, bubbles grow and start breaking up with the expansion of the bed. Under these conditions, the top surface of the bed is no longer distinguishable. In fast fluidization or pneumatic fluidization, particles are transported out of the bed and need to be recycled back into the reactor. No distinct bed surface is observed. Fluidized bed reactors have the following advantages:

Uniform Particle Mixing: Due to the intrinsic fluid-like behavior of the solid particulate material, fluidized beds do not experience poor mixing as in packed beds. The elimination of radial and axial concentration gradients also allows for better fluid-solid contact, which is essential for reaction efficiency and quality.

Uniform Temperature Gradients: Many chemical reactions require the addition or removal of heat. Local hot or cold spots within the reaction bed are avoided in a fluidized situation.

Ability to Operate Reactor Continuously: The fluidized bed nature of these reactors allows for the ability to continuously withdraw the products and introduce new reactants into the reaction vessel. On top of continuous operation of the chemical reactions, the fluidized bed allows also to continuously or at a given frequency withdraw solid material or add continuously or at a given frequency new fresh solid material thanks to the flowable solid particulate material. Heat can be produced by passing an electrical current through a conducting material that has sufficiently high resistivity (the resistor) to transform electricity into heat. Electrical resistivity (also called specific electrical resistance or volume resistivity, being an intrinsic property independent of shape and size) and its inverse, electrical conductivity, is a fundamental property of a material that quantifies how strongly it resists or conducts electric current (SI unit of electrical resistivity is the ohm-meter ($\Omega \cdot m$) and for conductivity Siemens per meter (S/m)).

When electricity is passed through a fixed bed of electrically conducting particulate solids, having a sufficient resistivity, the bed offers resistance to the flow of current; this resistance depends on many parameters, including the nature of the solid, the nature of the linkages among the particles within the bed, the bed voidage, the bed height, the electrode geometry, etc. If the same fixed bed is fluidized by passing gas, the resistance of the bed increases; the resistance offered by the conducting particles generates heat within the bed and can maintain the bed in isothermal conditions (termed an electrothermal fluidized bed or electrofluid reactor). In many high-temperature reactions, electrofluid reactors offer in situ heating during the reaction and are particularly useful for operating endothermic reactions and hence save energy because no external heating or transfer of heat is required. It is a prerequisite that at least part of the solid particulate material is electrically conducting but non-conducting solid particulates can be mixed and still result in enough heat generation. Such non-conducting or very high resistivity solids can play a catalytic role in the chemical conversion. The characteristics of the bed material determine the resistance of an electrothermal fluidized bed furnace; as this is a charge resistor type of heat generation, the specific resistivity of the particles affects the bed resistance. The size, shape, composition, and size distribution of the particles also influence the magnitude of the bed resistance. Also, when the bed is fluidized, the voids generated between the particles increases the bed resistance. The total resistance of the bed is the sum of two components, e.g. the electrode contact-resistance (i.e., the resistance between the electrode and the bed) and the bed resistance. A large contact-resistance will cause extensive local heating in the vicinity of the electrode while the rest of the bed stays rather cool. The following factors determine the contact-resistance: current density, fluidization velocity, type of bed material, electrode size and the type of material used for the electrodes. The electrode compositions can be advantageously metallic like iron, cast iron or other steel alloys, copper or a copper-based alloy, nickel or a nickel-based alloy or refractory like metal, intermetallics or an alloy of Zr, Hf, V, Nb, Ta, Cr, Mo, W or ceramic-like carbides, nitrides or carbon-based like graphite. The area of contact between the bed material and the electrodes can be adjusted, depending on the electrode submergence and the amount of particulate material in the fluidized bed. Hence, the electrical resistance and the power level can be manipulated by adjusting these variables. Advantageously, to prevent overheating of the electrodes compared to the fluidised bed, the resistivity of the electrode should be lower (and hence the joule heating) than of the particulate material of the fluidized bed. In a preferred embodiment, the electrodes can be cooled by passing a colder fluid inside or outside the electrodes. Such fluids can be any liquid that vaporises upon heating, gas stream or can be a part of the colder feedstock that first cools the electrode before entering the fluidised bed.

Bed resistance can be Predicted by the ohmic law. The mechanism of current transfer in fluidized beds is believed to occur through current flow along continuous chains of conducting particles at low operating voltages. At high voltages, a current transfer occurs through a combination of chains of conducting particles and arcing between the electrode and the bed as well as particle-to-particle arcings that might ionize the gas, thereby bringing down the bed resistance. Arcing inside the bed, in principle, is not desirable as it would lower the electrical and thermal efficiency. The gas velocity impacts strongly the bed resistance, a sharp increase in resistance from the settled bed onward when the gas flow rate is increased; a maximum occurred close to the incipient fluidization velocity, followed by a decrease at higher velocities. At gas flow rates sufficient to initiate slugging, the resistance again increased. Particle size and shape impact resistance as they influence the contacts points between particles. In general, the bed resistivity increases 2 to 5 times from a settled bed (e.g. 20 Ohm·cm for graphite) to the incipient fluidisation (60 Ohm·cm for graphite) and 10 to 40 times from a settled bed to twice (300 Ohm·cm for graphite) the incipient fluidisation velocity. Non or less-conducting particles can be added to conducting particles. If the conducting solid fraction is small, the resistivity of the bed would increase due to the breaking of the linkages in the chain of conducting solids between the electrodes. If the non-conducting solid fraction is finer in size, it would fill up the interstitial gaps or voidage of the larger conducting solids and hence increase the resistance of the bed.

In general, for a desired high heating power, a high current at a low voltage is preferred. The power source can be either AC or DC. Voltages applied in an electrothermal fluidized bed are typically below 100 V to reach enough heating power. The electrothermal fluidized bed can be controlled in the following three ways:

1. Adjusting the gas flow: Because the conductivity of the bed depends on the extent of voidage or gas bubbles inside the bed, any variation in the gas flow rate would change the power level; hence the temperature can be controlled by adjusting the fluidizing gas flow rate. The flow rate required for optimum performance corresponds to a velocity which equals or slightly exceeds the minimum fluidization velocity.
2. Adjusting the electrode submergence: The power level can also be controlled by varying the electrode immersion level inside the bed because the conductivity of the bed is dependent on the area of contact between the conducting particles and the electrode: the surface area of the electrode available for current flow increases with electrode submergence, leading to a reduction in overall resistance.
3. Adjusting the applied voltage: although changing the power level by using the first two methods is often more affordable or economical than increasing the applied voltage, however in electrothermal fluidized beds three variables are available to control the produced heating power.

The wall of the reactor is generally made of graphite, ceramics (like SiC), high-melting metals or alloys as it is versatile and compatible with many high-temperature reactions of industrial interest. The atmosphere for the reaction is often restricted to the neutral or the reducing type as an oxidising atmosphere can combust carbon materials or create a non-conducting metal oxide layer on top of metals or alloys. The wall and/or the distribution plate itself can act as an electrode for the reactor. The fluidized solids can be graphite, carbon, or any other high-melting-point, electrically conducting particles. The other electrodes, which is usually immersed in the bed, can also be graphite or a high-melting-point metal, intermetallics or alloys.

It may be advantaged to generate the required reaction heat by heating the conductive particles and/or catalyst particles in a separate zone of the reactor where little or substantially no methane feedstock is present, but only diluent gases. The benefit is that the appropriate conditions of fluidization to generate heat by passing an electrical current through a bed of conductive particles can be optimized whereas the optimal reaction conditions during methane transformation can be selected for the other zone of the reactor. Such conditions of optimal void fraction and linear velocity might be different for heating purposes and chemical transformation purposes.

In an embodiment of the present disclosure, the installation comprises of two zones arranged in series namely a first zone being a heating zone and a second zone being a reaction zone, where the conductive particles and catalyst particles are continuously moved or transported from the first zone to the second zone and vice versa. The first and second zones can be different parts of a fluidized bed or can be located in separate fluidized beds reactors connected one to each other.

In the said embodiment, the process to perform an endothermic methane pyrolysis reaction comprises the steps of:
 a) providing at least one fluidized bed reactor comprising at least two electrodes, a bed comprising particles, and optionally a solid discharge system;
 b) putting the particles of the bed in a fluidized state by passing upwardly through the said bed a fluid stream, to obtain a fluidized bed;
 c) heating the fluidized bed to a temperature ranging from 500° C. to 1200° C. to conduct the endothermic methane pyrolysis reaction to produce a reactor effluent comprising at least solid carbon, hydrocarbons having at least two carbons and hydrogen; and
 d) optionally, recovering from the reactor effluent produced at step (c) the hydrocarbons having at least two carbons and hydrogen;
wherein the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 800° C. wherein the catalytic composition comprises one or more metallic compounds, wherein the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof, and wherein the at least one fluidized bed reactor provided in step a) comprises a heating zone and a reaction zone and wherein the fluid stream provided in step b) is provided to the heating zone and comprises diluent gases and the step c) of heating the fluidized bed to a temperature ranging from 500° C. to 1200° C. to conduct the endothermic methane pyrolysis reaction comprises the following sub-steps:
 heating the fluidized bed to a temperature ranging from 500° C. to 1200° C. by passing an electric current through the heating zone of the at least one fluidized bed,
 transporting the heated particles from the heating zone to the reaction zone,
 in the reaction zone, putting the heated particles in a fluidized state by passing upwardly through the said bed of the reaction zone a fluid stream comprising a methane feedstock and optional diluent gases to obtain a fluidized bed and to conduct the endothermic methane pyrolysis reaction,
 optionally, recovering the particles from the reaction zone and recycling them to the heating zone.

For example, the diluent gases can be one or more selected from steam, air, methane, natural gas, hydrogen, carbon dioxide, argon, helium and nitrogen.

For example, the at least one fluidized bed reactor is at least two fluidized bed reactors connected one to each other wherein at least one of said at least two fluidized bed reactors is the heating zone and at least another of said at least two fluidized bed reactors is the reaction zone. With preference, the at least one fluidized bed reactor being the heating zone comprises gravitational or pneumatic transport means to transport the particles from the heating zone to the reaction zone and/or the installation comprises means arranged to inject a methane feedstock to the at least one fluidized bed reactor being the reaction zone. The installation is devoid of means to inject a methane feedstock to the at least one fluidized bed reactor being the heating zone.

For example, the at least one fluidized bed reactor comprising at least two electrodes and a bed comprising particles is devoid of packing.

For example, the at least one fluidized bed reactor is a single fluidized bed reactor wherein the heating zone is the bottom part of the fluidized bed reactor while the reaction zone is the top part of the fluidized bed reactor. With preference, the installation comprises means to inject a methane feedstock between the two zones.

Step c) provides that the endothermic methane pyrolysis reaction is performed on a methane feedstock which implies that a methane feedstock is provided. It is understood that the methane feedstock is provided to the reaction zone and that when the heating zone is separated from the reaction zone then, with preference, no methane feedstock is provided to the heating zone. It is understood that in addition to the methane feedstock provided to the reaction zone, steam can be provided to the reaction zone to reach the recommended steam to methane ratio in the reaction zone. When the heating zone and the reaction zone are mixed (i.e., the same zone); the fluid stream provided in step b) comprises a methane feedstock. The fluid stream may be a gaseous stream and/or a vaporized stream.

The Bed Comprising Particles

According to the disclosure the particles of the bed comprises electrically conductive particles and catalytic particles. For example, the catalytic particles are electrically conductive. For example, the electrically conductive particles are a mixture of catalytic particles and non-catalytic particles.

To achieve the required temperature necessary to carry out the methane pyrolysis reaction, at least 10 wt. % of the particles based on the total weight of the particles of the bed are electrically conductive and have a resistivity ranging from 0.001 Ohm·cm to 500 Ohm·cm at 800° C.

For example, the electrically conductive particles have a resistivity ranging from 0.005 to 400 Ohm·cm at 800° C., preferably ranging from 0.01 to 300 Ohm·cm at 800° C.; more preferably ranging from 0.05 to 150 Ohm·cm at 800° C. and most preferably ranging from 0.1 to 100 Ohm·cm at 800° C.

For example, the electrically conductive particles have a resistivity of at least 0.005 Ohm·cm at 800° C.; preferably of at least 0.01 Ohm·cm at 800° C., more preferably of at least 0.05 Ohm·cm at 800° C.; even more preferably of at least 0.1 Ohm·cm at 800° C., and most preferably of at least 0.5 Ohm·cm at 800° C.

For example, the electrically conductive particles have a resistivity of at most 400 Ohm·cm at 800° C.; preferably of at most 300 Ohm·cm at 800° C., more preferably of at most 200 Ohm·cm at 800° C.; even more preferably of at most 150 Ohm·cm at 800° C., and most preferably of at most 100 Ohm·cm at 800° C.

For example, the particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the electrically conductive particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the particles of a catalytic composition have an average particle size ranging from 5 to 300 μm as determined by sieving according to ASTM D4513-11, preferably ranging from 10 to 200 μm and more preferably ranging from 1 to 200 μm or from 30 to 150 μm.

The electrical resistance is measured by a four-probe DC method using an ohmmeter. A densified power sample is shaped in a cylindrical pellet that is placed between the probe electrodes. Resistivity is determined from the measured resistance value, R, by applying the known expression $\rho = R \times A/L$, where L is the distance between the probe electrodes typically a few millimetres and A the electrode area.

The solid particulate material can exhibit electronic, ionic or mixed electronic-ionic conductivity. The ionic bonding of many refractory compounds allows for ionic diffusion and correspondingly, under the influence of an electric field and appropriate temperature conditions, ionic conduction.

The electrical conductivity, σ, the proportionality constant between the current density j and the electric field E, is given by $$\sigma = j/E = \Sigma c_i \times Z_i q \times \mu_i$$

where $c_i$ is the carrier density (number=cm³), $\mu_i$ the mobility (cm²/Vs), and $Z^1 q$ the charge ($q=1.6\times10^{-19}$ C) of the ith charge carrier. The many orders of magnitude differences in σ between metals, semiconductors and insulators generally result from differences in c rather than μ. On the other hand, the higher conductivities of electronic versus ionic conductors are generally due to the much higher mobilities of electronic versus ionic species.

The most common materials that can be used for resistive heating can be subdivided into nine groups:
  (1) Metallic alloys for temperatures up to 1200-1400° C.,
  (2) non-metallic resistors like silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$) and tungsten silicide ($WSi_2$) up to 1600-1900° C.,
  (3) several mixed oxides and/or mixed sulphides with variable temperature optima,
  (4) carbons like graphite up to 2000° C.,
  (5) metallic carbides,
  (6) transition metal nitrides,
  (7) metallic phosphides,
  (8) superionic conductors and
  (9) phosphate electrolytes.

A first group of metallic alloys, for temperatures up to 1150-1250° C., is constituted by Ni—Cr alloys with low Fe content (0.5-2.0%), preferably alloy Ni—Cr (80% Ni, 20% Cr) and (70% Ni, 30% Cr). Increasing the content of Cr increases the material resistance to oxidation at high temperatures. A second group of metallic alloys having three components are Fe—Ni—Cr alloys, with maximum operating temperature in an oxidizing atmosphere to 1050-1150° C. but which can be conveniently used in reducing atmospheres or Fe—Cr—Al (chemical composition 15-30% Cr, 2-6% Al and Fe balance) protecting against corrosion by a surface layer of oxides of Cr and Al, in oxidizing atmospheres can be used up to 1300-1400° C. Silicon carbides can exhibit wide ranges of resistivity that can be controlled by the way they are synthesized and the presence of impurities like aluminium, iron, oxide, nitrogen or extra carbon or silicon resulting in non-stoichiometric silicon carbide. In general silicon carbide has a high resistivity at low temperature but has good resistivity in the range of 500 to 1200° C. In an alternative embodiment, the non-metallic resistor can be devoid of silicon carbide and/or can comprise molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof.

Graphite has rather low resistivity values, with a negative temperature coefficient up to about 600° C. after which the resistivity starts to increase.

Many mixed oxides and/or mixed sulphides, having in general too high resistivity at low temperature, become ionic or mixed conductors at high temperature. The following circumstances can make oxides sufficient conductors for heating purposes: ionic conduction in solids is described in terms of the creation and motion of atomic defects, notably vacancies and interstitials of which its creation and mobility is very positively dependent on temperature. Three mechanisms for ionic defect formation in oxides are known: (1) Thermally induced intrinsic ionic disorder (such as Schottky and Frenkel defect pairs resulting in non-stoichiometry), (2). Redox-induced defects and (3) Impurity-induced defects. The first two categories of defects are predicted from statistical thermodynamics and the latter form to satisfy electroneutrality. In the latter case, high charge carrier densities can be induced by substituting lower valent cations for the host cations. Mixed oxides and/or mixed sulphides with fluorite, pyrochlore or perovskite structure are very suitable for substitution by one or more lower-valent cations.

Several sublattice disordered oxides or sulphides have high ion transport ability at increasing temperature. These are superionic conductors, such as $LiAlSiO_4$, $LinoGeP_2S_{12}$, $Li_{3.6}Si_{0.6}P_{0.4}O_4$, NaSICON (sodium (Na) Super Ionic CONductor) with the general formula $Na_{1+x}Zr_2P_{3-x}Si_xO_{12}$ with $0<x<3$, for example Nasicon $Na_3Zr_2PSi_2O_{12}$ (x=2), or sodium beta alumina such as $NaAl_{11}O_{17}$, $Na_{1.6}Al_{11}O_{17.3}$, and/or $Na_{1.76}Li_{0.38}Al_{10.62}O_{17}$.

High concentrations of ionic carriers can be induced in intrinsically insulating solids and creating high defective solids. Thus, the electrically conductive particles of the bed comprise one or more mixed oxides being an ionic or mixed conductor, namely being doped with one or more lower-valent cations and/or one or more mixed sulphides being an ionic or mixed conductor, namely being doped with one or more lower-valent cations. With preference, the mixed oxides are selected from one or more oxides having a cubic fluorite structure being at least partially substituted with one or more lower-valent cations, preferentially selected from Sm, Gd, Y, Sc, Yb, Mg, Ca, La, Dy, Er, Eu; and/or from one or more $ABO_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more $ABO_3$-perovskites with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2O_7$-pyrochlores with A trivalent cation and B tetra-valent cation being at least partially substituted in A position with one or more lower-valent cations, preferentially selected from Ca or Mg, and comprising at least one of Sn, Zr and Ti in B position.

With preference, the mixed sulphide are selected from one or more sulphides having a cubic fluorite structure being at least partially substituted with one or more lower-valent cations, preferentially selected from Sm, Gd, Y, Sc, Yb, Mg, Ca, La, Dy, Er, Eu; and/or from one or more $ABS_3$ structures with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more $ABS_3$ structures with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2S_7$ structures with A trivalent cation and B tetra-valent cation being at least partially substituted in A position with one or more lower-valent cations, preferentially selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

Said one or more oxides having a cubic fluorite structure, said one or more $ABO_3$-perovskites with A and B tri-valent cations, said one or more $ABO_3$-perovskites with A bivalent cation and B tetra-valent cation, said one or more $A_2B_2O_7$-pyrochlores with A trivalent cation and B tetra-valent cation being at least partially substituted with lower valent cations, said one or more sulphides having a cubic fluorite structure, said one or more $ABS_3$ structures with A and B tri-valent cations, said one or more $ABS_3$ structures with A bivalent cation and B tetra-valent cation, said one or more $A_2B_2S_7$ structures with A trivalent cation and B tetra-valent cation being at least partially substituted with lower valent cations also means that the same element, being a high-valent cation, can be reduced in the lower-valent equivalent, for example, Ti(IV) can be reduced in Ti(III) and/or Co(III) can be reduced in Co(II) and/or Fe(III) can be reduced in Fe(II) and/or Cu(II) can be reduced in Cu(I).

Phosphate electrolytes such as $LiPO_4$ or $LaPO_4$ can also be used as electrically conductive particles.

Metallic carbides, transition metal nitrides and metallic phosphides can also be selected as electrically conductive particles. For example, metallic carbides are selected from iron carbide ($Fe_3C$), molybdenum carbide (such as a mixture of MoC and $Mo_2C$). For example, said one or more transition metal nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN). For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

For example, the electrically conductive particles of the bed are or comprise silicon carbide. For example, at least 10 wt. % of the particles based on the total weight of the particles of the bed are silicon carbide particles and have a resistivity ranging from 0.001 Ohm·cm to 500 Ohm·cm at of 800° C.

In the embodiment wherein the electrically conductive particles of the bed comprise silicon carbide, the person skilled in the art will have the advantage to conduct a step of pre-heating with a gaseous stream said fluidized bed reactor before conducting said endothermic reaction in the fluidized bed reactor. Advantageously, the gaseous stream is a stream of inert gas, i.e., nitrogen, argon, helium, methane, carbon dioxide, steam or a mixture thereof. The temperature of the gaseous stream can be at least 500° C., or at least 550° C., or at least 600° C., or at least 650° C., or at least 700° C., or at least 750° C., or at least 800° C., or at least 850° C., or at least 900° C. Advantageously, the temperature of the gaseous stream can be comprised between 500° C. and 900° C., for example between 600° C. and 800° C. or between 650° C. and 750° C. Said gaseous stream of inert gas can also be used as the fluidification gas. The pre-heating of the said gaseous stream of inert gas is performed thanks to conventional means, including using electrical energy. The temperature of the gaseous stream used for the pre-heating of the bed doesn't need to reach the temperature reaction.

Indeed, the resistivity of silicon carbide at ambient temperature is high, to ease the starting of the reaction, it may be useful to heat the fluidized bed by external means, as with preference the fluidized bed reactor is devoid of heating means. Once the bed is heated at the desired temperature, the use of a hot gaseous stream may not be necessary. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

However, in an embodiment, the electrically conductive particles of the bed comprise a mixture of silicon carbide particles and electrically conductive particles different from silicon carbide particles.

The pre-heating step may be also used in the case wherein electrically conductive particles different from silicon carbide particles are present in the bed. For example, it may be used when the content of silicon carbide in the electrically conductive particles of the bed is more than 80 wt. % based on the total weight of the electrically conductive particles of the bed, for example, more than 85 wt. %, for example, more than 90 wt. %, for example, more than 95 wt. %, for example, more than 98 wt. %, for example, more than 99 wt. %. However, a pre-heating step may be used whatever is the content of silicon carbide particles in the bed.

In the embodiment wherein the electrically conductive particles of the bed comprise a mixture of silicon carbide particles and electrically conductive particles different from silicon carbide particles, the electrically conductive particles of the bed may comprise from 10 wt. % to 99 wt. % of silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed comprise a mixture of silicon carbide particles and electrically conductive particles different from silicon carbide particles and the electrically conductive particles of the bed comprises at least 40 wt. % of silicon carbide particles based on the total weight of the electrically conductive particles of the bed; preferably at least 50 wt. %, more preferably at least 60 wt. %, even more preferably at least 70 wt. % and most preferably at least 80 wt. %.

In an embodiment, the electrically conductive particles of the bed may comprise from 10 wt. % to 90 wt. % of electrically conductive particles different from silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

However, it may be interesting to keep the content of electrically conductive particles different from silicon carbide particles quite low in the mixture. Thus, in an embodiment, the electrically conductive particles of the bed comprise a mixture of silicon carbide particles and electrically conductive particles different from silicon carbide particles and electrically conductive particles of the bed comprises from 1 wt. % to 20 wt. % of electrically conductive particles different from silicon carbide based on the total weight of the electrically conductive particles of the bed; preferably, from 2 wt. % to 15 wt. %, more preferably, from 3 wt. % to 10 wt. %, and even more preferably, from 4 wt. % to 8 wt. %.

For example, the electrically conductive particles of the bed comprise a mixture of silicon carbide particles and electrically conductive particles different from silicon carbide particles and the said electrically conductive particles different from silicon carbide particles are particles selected from graphite.

Thus, in an embodiment, the electrically conductive particles are a combination of silicon carbide particles and graphite particles. Such electrically conductive particles, upon the electrification of the fluidized bed reactor, will heat up and because of their fluidification, will contribute to the raise and/or to the maintaining of the temperature within the reactor. The Joule heating of such electrically conductive material allows accelerating the heating of the reactant and/or of the catalyst that is present within the fluidized bed reactor.

When graphite is selected, it can preferably be flake graphite. It is also preferable that the graphite has an average particle size ranging from 1 to 400 μm, as determined by sieving according to ASTM D4513-11, preferably from 5 to 300 μm, more preferably ranging from 10 to 200 μm and most preferably ranging from 20 to 200 μm or from 30 to 150 μm.

The presence of electrically conductive particles different from silicon carbide particles in the bed allows applying the process according to the disclosure with or without the pre-heating step, preferably without the pre-heating step. Indeed, the electrically conductive particles, upon the electrification of the fluidized bed reactor, will heat up and because of their fluidification, will contribute to raising and/or maintaining the desired temperature within the reactor.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

In an embodiment, the electrically conductive particles are devoid of graphite and/or carbon black. In an embodiment, the electrically conductive particles are devoid of coke and/or petroleum coke.

The Silicon Carbide Particles

For example, the silicon carbide is selected from sintered silicon carbide, nitride-bounded silicon carbide, recrystallised silicon carbide, reaction bonded silicon carbide and any mixture thereof.

Sintered SiC (SSiC) is a self-bonded material containing a sintering aid (typically boron) of less than 1% by weight.

Recrystallized silicon carbide (RSiC), a high purity SiC material sintered by the process of evaporation—condensation without any additives.

Nitride-bonded silicon carbide (NBSC) is made by adding fine silicon powder with silicon carbide particles or eventually in the presence of a mineral additive and sintering in a nitrogen furnace. The silicon carbide is bonded by the silicon nitride phase ($Si_3N_4$) formed during nitriding.

Reaction bonded silicon carbide (RBSC), also known as siliconized silicon carbide or SiSiC, is a type of silicon carbide that is manufactured by a chemical reaction between porous carbon or graphite with molten silicon. The silicon reacts with the carbon forming silicon carbide and bonds the silicon carbide particles. Any excess silicon fills the remaining pores in the body and produces a dense SiC—Si composite. Due to the left-over traces of silicon, reaction bonded silicon carbide is often referred to as siliconized silicon carbide. The process is known variously as reaction bonding, reaction sintering, self-bonding, or melt infiltration.

In general, high purity SiC particles have a resistivity above 1000 Ohm·cm, whereas sintered, reaction bonded and nitride-bonded can exhibit resistivities of about 100 to 1000 depending on the impurities in the SiC phase. Electrical resistivity of bulk polycrystalline SiC ceramics shows a wide range of resistivity depending on the sintering additive and heat-treatment conditions (Journal of the European Ceramic Society, Volume 35, Issue 15, December 2015, Pages 4137; Ceramics International, Volume 46, Issue 4, March 2020, Pages 5454). SiC polytypes with high purity possess high electrical resistivity ($>10^6$ Ω·cm) because of their large bandgap energies. However, the electrical resistivity of SiC is affected by doping impurities. N and P act as n-type dopants and decrease the resistivity of SiC, whereas Al, B, Ga, and Sc act as p-type dopants. SiC doped with Be, O, and V are highly insulating. N is considered the most efficient dopant for improving the electrical conductivity of SiC. For N doping of SiC (to decrease resistivity) $Y_2O_3$ and $Y_2O_3$-$REM_2O_3$(REM=rare earth metal=Sm, Gd, Lu) have been used as sintering additives for efficient growth of conductive SiC grains containing N donors. N-doping in SiC grains was promoted by the addition of nitrides (AlN, BN, $Si_3N_4$, TiN, and ZrN) or combinations of nitrides and $REM_2O_3$(AlN-$REM_2O_3$(REM=rare earth metal=Sc, Nd, Eu, Gd, Ho, and Er) or TiN—$Y_2O_3$).

The Catalytic Composition

The pyrolysis reaction is conducted by contacting the methane feedstock within the fluidized bed reactor comprising particles of a catalytic composition.

For example, the content of the particles of a catalytic composition based on the total weight of the particle of the bed is ranging from 10 wt. % to 100 wt. %; preferably from 15 wt. % to 99 wt. %, more preferably from 20 wt. % to 95 wt. %, more preferably from 35 wt. % to 90 wt. %, even more preferably from 40 wt. % to 85 wt. %, most preferably from 45 wt. % to 80 wt. % and even most preferably from 50 wt. % to 75 wt. %. In the case where the content of the particles of a catalytic composition based on the total weight of the particles of the bed is 100 wt. %, said particles of a catalytic composition are also electrically conductive particles For such a methane dehydrogenation reaction, any dehydrocyclization catalyst known in the art could be used. For example, the catalytic composition comprises one or more metallic compounds selected from Ca, Mg, Ba, Y, La, Sc, Ce, Ti, Zr, Hf, V, Nb, Ta, Cr, Mo, W, Mn, Re, Fe, Ru, Co, Rh, Ir, Ni, Pd, Cu, Ag, Au, Zn, Al, Ga, Si, Ge, In, Sn, Pb, or Bi or transuranium metals. For example, the catalytic composition comprises one or more metallic compounds selected from Ca, Mg, Ba, Y, La, Sc, Ce, Ti, Zr, Hf, V, Nb, Ta, Cr, Mo, W, Mn, Re, Fe, Ru, Co, Rh, Ir, Ni, Pd, Cu, Ag, Au, Zn, Al, Ga, Si, Ge, In, Sn, Pb, or Bi. With preference, one or more metallic compounds selected from Fe, Mo, W or Re; more preferably the one or more metallic compounds are selected from Fe, Mo and W; even more preferably the one or more metallic compounds are selected from Mo and/or W, and most preferably the metallic compound is Mo. These metallic compounds can be under a metallic form (i.e. the elemental form) and/or under one or more forms of metal oxide, carbide, nitride or phosphides, preferably under the form of carbide. These elements can be supported or not.

Platinum and osmium can also be used but, in general, are not preferred.

Optionally, the catalytic composition comprises boron.

The Catalytic Support of the Catalyst Composition

When the catalyst composition comprises a catalytic support, said catalytic support is either amorphous or crystalline and in particular may be selected from oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements; more preferably from $Al_2O_3$. Alternatively, or also, the catalyst support is one or more porous materials, such as carbon black, activated carbon, graphite, carbon fibers, biochar, carbon nanotubes, carbon xerogels, graphene, one or more microporous crystalline materials like one or more zeolites or a mesoporous material.

Preferred support materials are those common materials (mentioned above) that can be used for resistive heating at the same time and which can be subdivided into metallic alloys and non-metallic resisters liked silicon carbide (SiC)

and molybdenum disilicide (MoSi₂), several mixed oxides with variable temperature optime and carbons like graphite. This latter option results in intimate contact between the catalytic active metal and the resistor particulate material. In addition, the catalytic support may be a porous material, such as a microporous crystalline material like a zeolite or a mesoporous material. As used herein the term "microporous" refers to pores having a diameter of less than 2 nm, whereas the term "mesoporous" refers to pores having a diameter of from 2 to 50 nm.

For example, the catalyst support of the catalytic composition is one or more zeolites, preferably in a content of at least 60 wt. % based on the total molar content of the catalyst composition, more preferably at least 70 wt. %, even more preferably at least 80 wt. %, most preferably at least 90 wt. %. The one or more zeolites have a crystalline aluminosilicate oxide framework substituted with a metal, said metal being preferably selected from Fe, Sn, Hf, Zn, Zr, Ti, V, Ta, Ga, Ge, Nb, Mn, Mo, W, Co, and/or Cd. In other words, the one or more zeolites are one or more microporous crystalline materials that are advantageously selected from silicates, aluminosilicates, titanosilicates, titanoaluminosilicates, aluminophosphates, metallophosphates, metalloaluminophosphates, and/or silicoaluminophosphates. The metal component can be dispersed on the inorganic support by any means well-known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

When steaming is performed, the one or more zeolites are subjected to a step of steaming before step (c) of the process. With preference, the step of steaming is conducted at a temperature ranging between 400° C. and 1000° C., more preferably between 450° C. and 950° C., even more preferably between 500° C. and 900° C.; and/or at a pressure of 0.01 MPa or more.

For example, the one or more zeolites have a crystalline alumino-silicate oxide framework substituted with phosphorus.

For example, the one or more zeolites have a crystalline alumino-silicate oxide framework comprising tin, molybdenum, tungsten, and/or iron in the tetrahedral sites of the framework.

For example, the one or more zeolites have a molar ratio of silicon over the sum between the amount of the aluminium and the metallic element (i.e. a Si/(Al+M) (M=metal) molar ratio) of at least 5, preferably of at least 10, more preferably of at least 20, even more preferably of at least 50, most preferably of at least 100. For example, the one or more zeolites have a molar ratio of silicon over the sum between the amount of the aluminium and the metallic element (i.e. a Si/(Al+M) (M=metal) molar ratio) ranging between 5 and 1000, preferably between 10 and 900, more preferably between 20 and 800, even more preferably between 50 and 700, most preferably between 100 and 600.

For example, the one or more zeolites have a crystalline alumino-silicate oxide framework with an anionic charge which is advantageously balanced by cationic elements selected from H, Li, Na, K, Cs, Mg, Ca, Sr, Ba, La and/or Ce. For example, the one or more zeolites are in a sodium form, in a protonic form or in a protonic/sodium form. Advantageously, the one or more zeolites are modified by ion-exchange or by impregnation with one or more alkali metal cations, such as Li, K, and/or Cs; and/or with one or more alkali-earth metal cations, such as Mg, Ca, Sr, or Ba; and/or with one or more transition metal cations, such as Fe, Ni, Cu, Mn, V, W; and/or with one or more rare-earth metal cations, such as La or Ce. Such subsequent ion exchange or impregnation may replace the charge-balancing counterions, but furthermore may also partially replace ions in the oxide framework resulting in a modification of the crystalline make-up and structure of the oxide framework.

It is preferred that the one or more zeolites are synthesized without an organic template.

With preference, the one or more zeolites are selected from the list comprising AEL, AFI, AFO, BEA, CHA, ERI, FAU, FER, ITE, ITH, IWR, IWS, IWW, KFI, LEV, LTL, MEL, MFI, MFS, MOR, MSE, MTT, MTW, MWW, TON and/or VFI families. More preferably, the zeolite is a zeolite from the MFI family.

When the zeolite is selected from the AEL family, the zeolite is or comprises SAPO-11.

When the zeolite is selected from the AFI family, the zeolite is or comprises ALPO-5.

When the zeolite is selected from the AFO family, the zeolite is or comprises SAPO-41.

When the zeolite is selected from the BEA family, the zeolite is or comprises zeolite beta.

When the zeolite is selected from the CHA family, the zeolite is or comprises SAPO-34.

When the zeolite is selected from the ERI family, the zeolite is or comprises SAPO-17.

When the one or more zeolites are selected from the FAU family, the one or more zeolites are preferably one or more selected from zeolite X, zeolite Y, ultrastabilized zeolite Y and dealuminized zeolite Y.

When the zeolite is selected from the FER family, the zeolite is or comprises ZSM-35.

When the zeolite is selected from the ITE family, the zeolite is or comprises ITQ-3.

When the zeolite is selected from the ITH family, the zeolite is or comprises ITQ-13.

When the zeolite is selected from the IWR family, the zeolite is or comprises ITQ-24.

When the zeolite is selected from the IWR family, the zeolite is or comprises ITQ-26.

When the zeolite is selected from the IWW family, the zeolite is or comprises ITQ-22.

When the zeolite is selected from the KFI family, the zeolite is or comprises ZK-5.

When the zeolite is selected from the LEV family, the zeolite is or comprises SAPO-35.

When the zeolite is selected from the LTL family, the zeolite is or comprises zeolite L.

When the zeolite is selected from the MEL family, the zeolite is or comprises ZSM-11.

When the one or more zeolites are selected from the MFI family, the one or more zeolites are preferably one or more selected from ZSM-5, TS-1, TS-2 and silicalite, more preferably, the zeolite is ZSM-5.

When the zeolite is selected from the MFS family, the zeolite is or comprises ZSM-57.

When the zeolite is selected from the MOR family, the zeolite is or comprises mordenite.

When the zeolite is selected from the MSE family, the zeolite is or comprises MCM-68.

When the zeolite is selected from the MTT family, the zeolite is or comprises ZSM-23.

When the zeolite is selected from the MTW family, the zeolite is or comprises ZSM-12.

When the one or more zeolites are selected from the MWW family, the one or more zeolites are preferably one or more selected from MCM-22, PSH-3, SSZ-25, ERB-I, ITQ-I, ITQ-2, MCM-36, MCM-49 and MCM-56.

When the zeolite is selected from the TON family, the zeolite is or comprises ZSM-22.

When the zeolite is selected from the VFI family, the zeolite is or comprises VPI-5.

For example, the catalyst support of the catalytic composition can be one or more mesoporous materials, preferably in a content of at least 60 wt. % based on the total molar content of the catalytic composition, more preferably at least 70 wt. %, even more preferably at least 80 wt. %, most preferably at least 90 wt. %. In this case, the one or more mesoporous materials are advantageously selected from MCM-41, MCM-48, MCM-50, FSM-16 and/or SBA-15.

Examples of preferred catalysts include iron, molybdenum, tungsten, rhenium and compounds and combinations thereof on an MFI zeolite, such as ZSM-5, or on silica ($SiO_2$) or alumina ($Al_2O_3$).

The particulate catalyst support particles preferably have a particle size 5-300 μm as determined by sieving according to ASTM D4513-11, more preferably between 10 and 200 μm and most preferably between 20 and 200 μm or between 30 and 150 μm. Metal contents on the support may be in the range 0.1-60.0 wt. %.

As the pyrolysis of methane is endothermic, the reaction tends to deposit coke on the catalyst and hence, to maintain the activity of the catalyst, a second portion of the catalyst is withdrawn from the reaction zone, either on an intermittent, or more preferably, a continuous basis, and transferred to a separate regeneration zone. The regeneration of catalyst could be performed by coke removal via burning or by coke graphitization.

The concentration of steam during the zeolite steam treatment in the flow is between 1 to 100%, more preferably from 5 to 50% of steam. The diluent is a gas selected from the group of nitrogen, argon, helium, air, natural gas, methane, $CO_2$, hydrogen, or steam or a mixture of thereof. The steam treatment is preferably carried out for a period of from 0.1 to 200 hours, more preferably from 0.2 hours to 24 hours. The steam treatment tends to reduce the amount of tetrahedral aluminium in the crystalline silicate framework, by forming alumina. The particular effect consists in reducing the strong Brønsted acidity of the zeolites.

The formation of extra-framework Al species is known to affect the pore structure and the porosity of the zeolite. Therefore, the removal of a large fraction of Al from the lattice leads to rearrangements of Si-T (tetrahedron) atoms and hence to the generation of large voids in the structure. The presence of such pores is crucial to obtain a high catalytic activity. Moreover, less aluminium also contributes to low coke formation and low ageing rates.

Optionally, following the steam treatment, an extraction step is performed to remove the partially dislodged alumina species by leaching. The leaching is performed by a monoprotic acid selected from the HCl, $HNO_3$, HBr, acetic, oxalic or formic or with a complexing agent which tends to form a soluble complex with alumina. The complexing agent is preferably in an aqueous solution thereof. The complexing agent may comprise an organic acid such as citric acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. A particularly preferred complexing agent may comprise an amine, preferably ethylene diamine tetraacetic acid (EDTA) or a salt thereof, in particular the sodium salt thereof.

Preferentially, these metals are used to substitute one or more aluminium atoms in the zeolite framework. Metal-substituted zeolites have weaker acidic sites.

Shaping of the One or More Zeolites with a Binder

According to the disclosure, the one or more zeolites can be shaped with a binder, which is an inorganic material, and preferentially silica or alumina. The zeolites shaped with the binder forms a catalyst composition, and the catalyst composition of the present disclosure preferably comprises at least 5 wt. % of a binder, at most 40 wt. % as based on the total weight of the catalyst composition and at most 40 wt. %. Typically, the catalyst composition of the present disclosure comprises between 20 wt. % and 25 wt. % to at most 80 wt. % of a binder as based on the total weight of the catalyst composition.

The preferred binder is selected from silica, alpha-alumina, clays, alumina phosphates, calcium phosphates, magnesium phosphates, and mullite. Most preferentially, the binder is silica. When present, the binder is in an amount of at least 10 wt. % as based on the total weight of the catalyst composition; preferably in an amount of at least 20 wt. %, most preferably in an amount of 30 wt. %, even more preferably in an amount of at least 40 wt. %, and most preferably in an amount of at least 50 wt. %.

Non-limiting examples of silicon sources suitable for the binder of the catalyst composition include silicates, precipitated silicas, for example, Zeosil® available from Rhodia, fumed silicas, for example, Aerosil® 200 available from Degussa Inc., New York, N.Y., silicon compounds such as tetraalkyl orthosilicates, for example, tetramethyl orthosilicate (TMOS) and tetraethylorthosilicate (TEOS), colloidal silicas or aqueous suspensions thereof, for example, Ludox® HS-40 available from E.I. du Pont de Nemours, Wilmington, Del., silicic acid, alkali-metal silicate, or any combination thereof. Other suitable forms of amorphous silica include silica powders, such as Ultrasil® VN3 SP (commercially available from Degussa). Other non-limiting examples of a suitable solid silica source are special granulated hydrophilic fumed silicas, mesoporous silica and high surface area precipitated silica SIPERNAT® from Evonik, Hi-Sil 233 EP (available from PPG Industries) and Tokusil (available from Tokuyama Asia Pacific).

In addition, suitable amorphous silica sources include silica sols, which are stable colloidal dispersions of amorphous silica particles in an aqueous or organic liquid medium, preferably water. Non-limiting examples of commercially available silica sols include those sold under the tradenames Nyacol® (available from Nyacol Nano Technologies, Inc. or PQ Corp.), Nalco (available from Nalco Chemical Company), Ultra-Sol (available from RESI Inc), Ludox® (available from W.R. Grace Davison), NexSil™ (available from NNTI). Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non-limiting examples of silica sols that contain no detectable traces of sodium include Bindzil® 2034D1, Levasil® 200, Nalco 1034A, Ultra-Sol 7H or NexSil™ 20A. In some case, silica dispersion prepared with alkylammonium might be useful. Non-limiting examples of commercially low sodium silica sols stabilized by ammonia or alkylammonium cations include LUDOX® TMA (available from W.R. Grace Davison) or VP WR 8520 from Evonik. The silica sols with higher $SiO_2$ content than 30 wt. % and even up to 50 wt. %, for example, W1250, W1836, WK341, WK7330 from Evonik are particularly preferred. The preferred source of silicon is a silica sol or a combination of silica sol with precipitated or fumed silica.

The Installation

The terms "bottom" and "top" are to be understood with the general orientation of the installation or the fluidized bed reactor. Thus, "bottom" will mean greater ground proximity than "top" along the vertical axis. In the different figures, the same references designate identical or similar elements.

Figure 1:
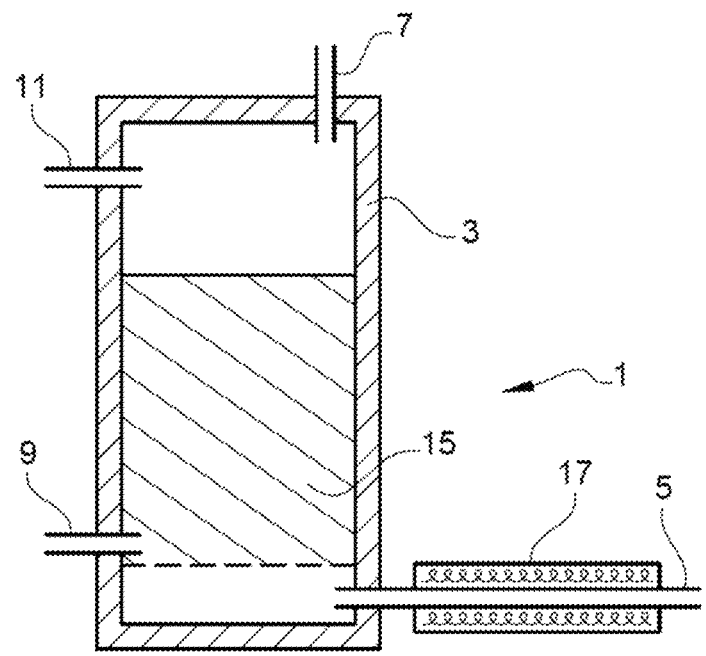
FIG. 1 illustrates an installation according to the prior art.

FIG. 1 illustrates a prior art fluidized bed reactor 1 comprising a reactor vessel 3, a bottom fluid nozzle 5 for the introduction of a fluidizing gas and a methane feedstock, an optional inlet 7 for the material loading, an optional outlet 9 for the material discharge and a gas outlet 11 and a bed 15. In the fluidized bed reactor 1 of FIG. 1 the heat is provided by preheating the feedstock by combustion of fossil fuels using heating means 17 arranged for example at the level of the line that provides the reactor with the fluidizing gas and the methane feedstock.

The installation of the present disclosure is now described with reference to FIGS. 2 to 5. For sake of simplicity, internal devices are known by the person in the art and are used in fluidized bed reactors, like bubble breakers, deflectors, particle termination devices, cyclones, ceramic wall coatings, thermocouples, etc. . . . are not shown in the illustrations.

However, it is preferred that the at least one fluidized bed reactor comprising at least two electrodes and a bed comprising particles is devoid of packing.

Figure 2:
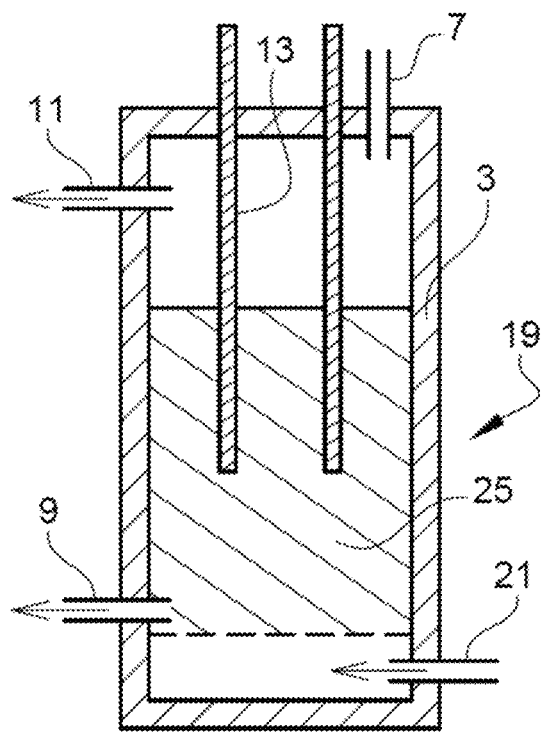
FIG. 2 illustrates an installation according to the disclosure with one reactor wherein the heating zone and reaction zone are the same.

FIG. 2 illustrates a first installation with a fluidized bed reactor 19 where the heating and reaction zone are the same. The fluidized bed reactor 19 comprises a reactor vessel 3, a bottom fluid nozzle 21 for the introduction of a fluidizing gas and a methane feedstock, an optional inlet 7 for the material loading, an optional outlet 9 for the material discharge and a gas outlet 11. The fluidized bed reactor 1 of FIG. 19 shows two electrodes 13 submerged in the bed 25.

Figure 3:
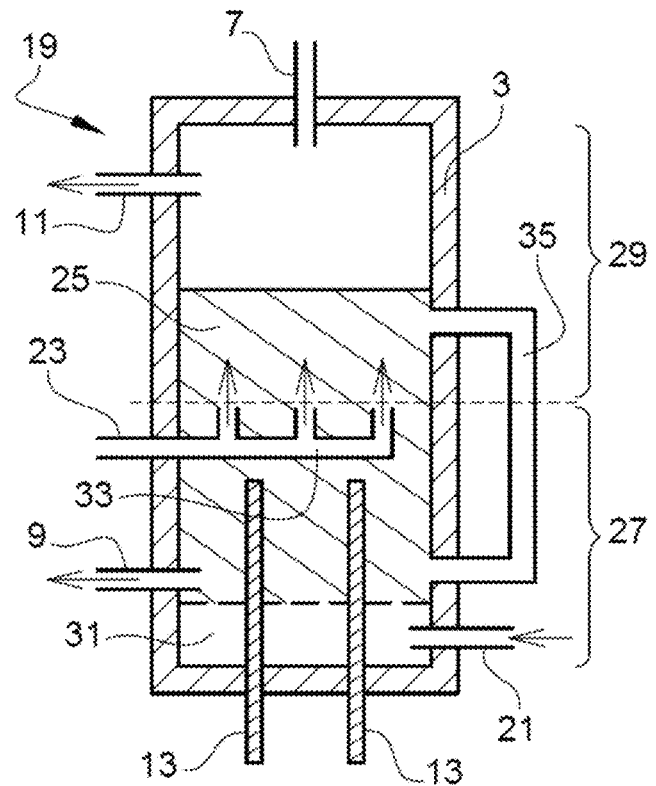
FIG. 3 illustrates an installation according to the disclosure with one reactor wherein the heating zone and reaction zone are arranged one above the other.

FIG. 3 illustrates an embodiment wherein at least one fluidized bed reactor 19 comprises a heating zone 27 and a reaction zone 29 with the heating zone 27 is the bottom zone and the reaction zone 29 is on top of the heating zone 27. One or more fluid nozzles 23 to provide a methane feedstock to the reaction zone from a distributor 33. As it can be seen in FIG. 3, the one or more fluid nozzles 23 can be connected to a distributor 33 to distribute the methane feedstock inside the bed 25.

Figure 4:
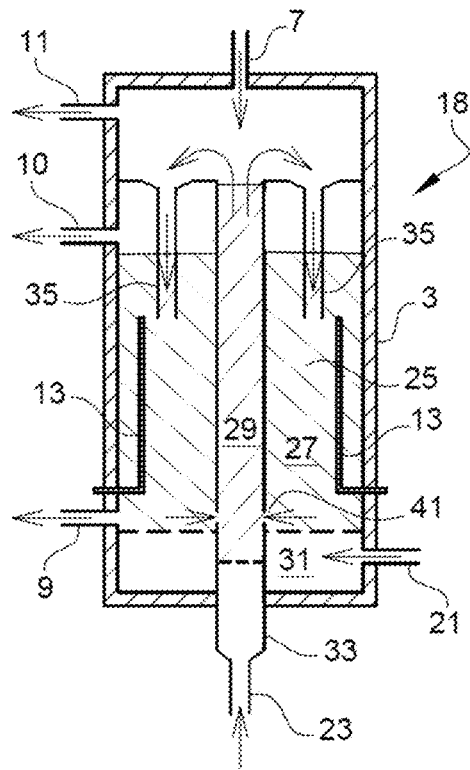
FIG. 4 illustrates an installation according to the disclosure with one reactor wherein the heating zone and reaction zone are arranged one lateral to the other.

FIG. 4 illustrates an installation wherein at least one fluidized bed reactor 18 comprises at least two lateral zones with the outer zone being the heating zone 27 and the inner zone being the reaction zone 29. The heated particles of the bed 25 from the outer zone are transferred to the inner zone by one or more openings 41 and mixed with the methane feedstock and optionally steam. At the end of the reaction zone, the particles are separated from the reaction product and transferred to the heating zone.

Figure 5:
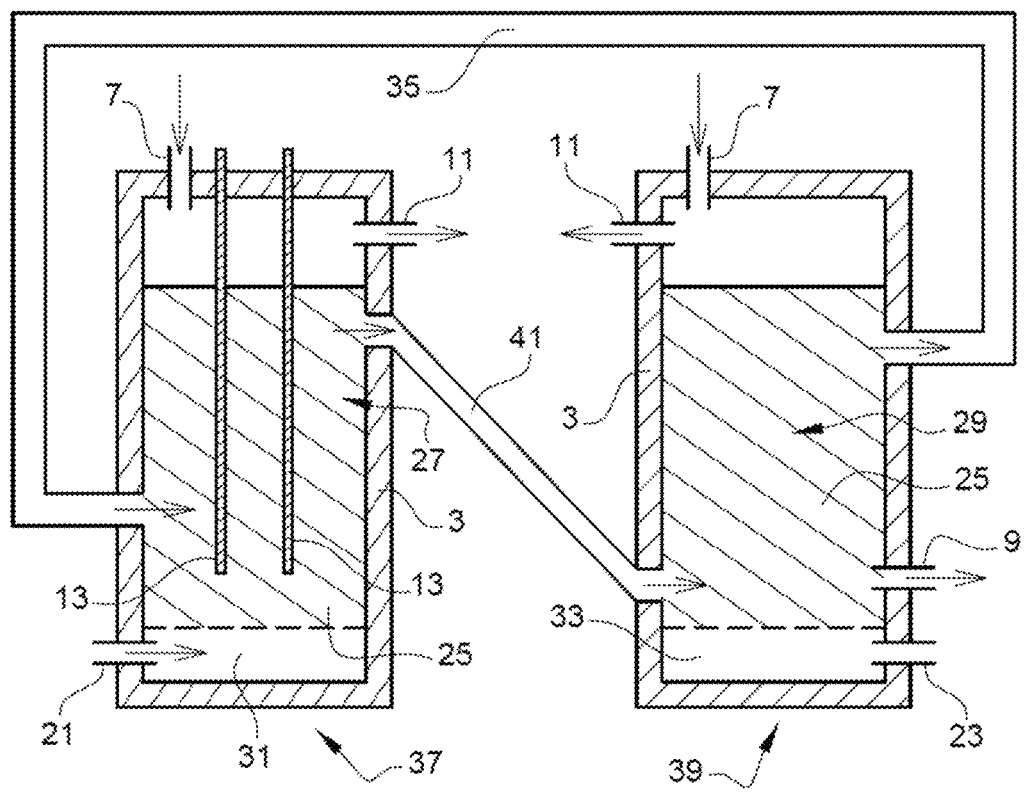
FIG. 5 illustrates an installation according to the disclosure with two reactors.
Figure 6:
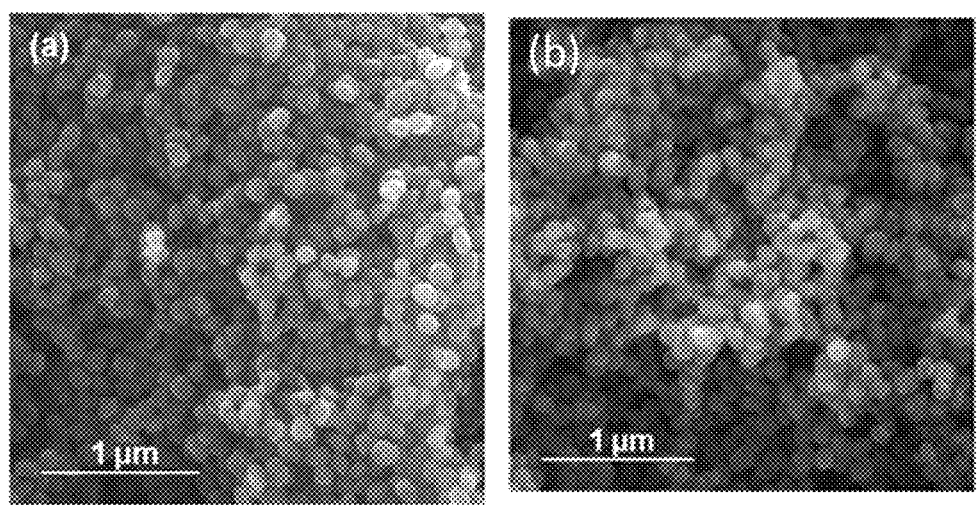
FIG. 6 represents SEM pictures of (a) a Mo-containing MFI zeolite and (b) SiMFI zeolite. The crystal size and morphology correspond to the one from purely siliceous MFI zeolite (silicalite-1) that would be obtained by using the same synthesis procedure without the addition of molybdenum (FIG. 6b).
Figure 7:
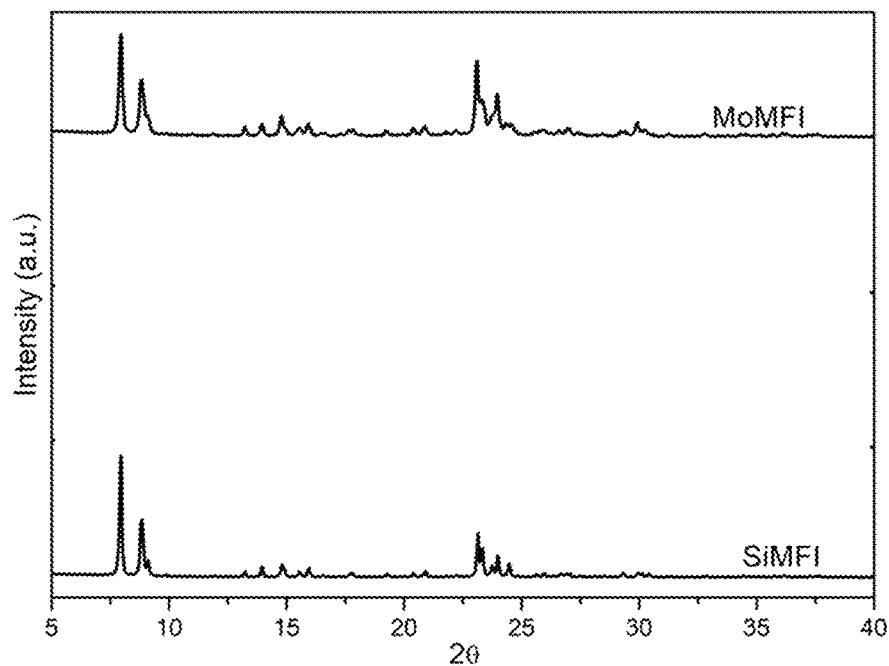
FIG. 7 corresponds to the XRD diffraction patterns of MoMFI and SiMFI samples obtained after a calcination step in the range 3 to 40° 2θ. Only Bragg peaks corresponding to MFI structure are present in all zeolite materials, more specifically, only peaks corresponding to the monoclinic MFI unit cell are observed when it would be expected to have orthorhombic symmetry if only purely siliceous MFI was to be obtained. The monoclinic symmetry can be easily evidenced by the splitting of some diffraction peaks (mainly at 23.30, 23.75, and 24.50° 2θ). Moreover, an expansion of unit cell volume was observed for all samples once compared to purely siliceous silicalite-1 zeolite. Both observations are indicating the presence of heteroatoms (Mo) in the framework of MFI structure. Details of the Le Bail profile refinement fits are presented in Table 1.

FIG. 5 illustrates the installation that comprises at least two fluidized bed reactors (37, 39) connected one to each other wherein at least one fluidized bed reactor is the heating zone 27 and one at least one fluidized bed reactor is the reaction zone 29.

The present disclosure provides for an installation to be used in a process to perform endothermic methane pyrolysis reaction, said installation comprises at least one fluidized bed reactor (18, 19, 37, 39) comprising:
  at least two electrodes 13,
  a reactor vessel 3;
  optionally, a solid discharge system
    one or more fluid nozzles (21; 23) for the introduction of a fluidizing gas and/or of a methane feedstock within at least one fluidized bed reactor (18, 19, 37, 39); and
  a bed 25 comprising particles;
  wherein the particles of the bed 25 comprise electrically conductive particles and particles of a catalytic composition and wherein at least 10 wt. % of the particles of the bed based on the total weight of the particles of the bed 25 are electrically conductive and have a resistivity ranging from 0.001 Ohm·cm to 500 Ohm·cm at 800° C., wherein the catalytic composition comprises one or more metallic compounds, and wherein the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphide being doped with one or more lower-valent cations, and/or any mixture thereof.

For example, one electrode is a submerged central electrode or two electrodes 13 are submerged within the reactor vessel 3 of at least one reactor (18, 19, 37).

The optional one or more solid discharge systems are systems that allow removing the carbon which is generated during the reaction. This can work by classification, namely based on particle size or particle density. Common classifier types are vibratory and rotary screeners, which classify materials by particle size, and cyclones, elutriation classifiers, and dynamic air classifiers, which classify materials by particle density.

For example, the fluidizing gas is one or more diluent gases.

In a preferred embodiment, the at least one fluidized bed reactor (18, 19, 37, 39) is devoid of heating means. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

For example, the reactor vessel 3 has an inner diameter of at least 100 cm, or at least 200 cm; or at least 400 cm. Such a large diameter allows to carry out the chemical reaction at an industrial scale, for example at a weight hourly space velocity of said reaction stream comprised between 0.1 $h^{-1}$ and 100 $h^{-1}$, preferably comprised between 1.0 $h^{-1}$ and 50 $h^{-1}$, more preferably comprised between 1.5 $h^{-1}$ and 10 $h^{-1}$, even more preferably comprised between 2.0 $h^{-1}$ and 6.0 $h^{-1}$. The weight hourly space velocity is defined as the ratio of mass flow of the reaction stream to the mass of solid particulate material in the fluidized bed.

The at least one fluidized bed reactor (18, 19, 37) comprises at least two electrodes 13. For example, one electrode is in electrical connection with the outer wall of the fluidized bed reactor, while one additional electrode is submerged into the fluidized bed 25, or both electrodes 13 are submerged into the fluidized bed 25. Said at least two electrodes 13 are electrically connected and can be connected to a power supply (not shown). It is advantageous that said at least two electrodes 13 are made of carbon-containing material. The person skilled in the art will have an advantage that the electrodes 13 are more conductive than the particle bed 25.

For example, at least one electrode 13 is made of or comprises graphite; preferably, all or the two electrodes 13 are made of graphite. For example, one of the electrodes is the reactor tube, so that the reactor comprises two electrodes, one being the submerged central electrode and one being the reactor tube.

For example, the at least one fluidized bed reactor comprises at least one cooling device arranged to cool at least one electrode.

During use of the fluidized bed reactor, an electric potential of at most 300 V is applied, preferably at most 250 V, more preferably at most 200 V, even more preferably at most 150 V, most preferably at most 100 V, even most preferably at most 90 V, or at most 80 V.

Thanks to the fact that the power of the electric current can be tuned, it is easy to adjust the temperature within the reactor bed.

The reactor vessel 3 can be made of graphite. In an embodiment, it can be made of electro-resistive material that is silicon carbide or a mixture of silicon carbide and one or more carbon-containing materials.

With preference, the reactor vessel 3 comprises reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ). SiAlON ceramics are ceramics based on the elements silicon (Si), aluminium (Al), oxygen (O) and nitrogen (N). They are solid solutions of silicon nitride ($Si_3N_4$), where Si—N bonds are partly replaced with Al—N and Al-O bonds.

For example, the reactor vessel 3 is made of an electro-resistive material that is a mixture of silicon carbide and one or more carbon-containing materials; and the electro-resistive material of the reactor vessel 3 comprises from 10 wt. % to 99 wt. % of silicon carbide based on the total weight of the electro-resistive material; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the reactor vessel 3 is made of an electro-resistive material that is a mixture of silicon carbide and one or more carbon-containing materials; and the one or more carbon-containing materials are selected from graphite, carbon black, coke, petroleum coke and/or any mixture thereof; with preference, the carbon-containing material is or comprises graphite and/or carbon black.

For example, the reactor vessel 3 is not conductive. For example, the reactor vessel 3 is made of ceramic.

For example, the at least one fluidized bed reactor (18, 19, 37, 39) comprises a heating zone 27 and a reaction zone 29, one or more fluid nozzles 21 to provide a fluidizing gas to at least the heating zone from a distributor 31, one or more fluid nozzles 23 to provide a methane feedstock to the reaction zone from a distributor 33, and means 41 to transport the particles from the heating zone 27 to the reaction zone 29 when necessary, and optional means 35 to transport the particles from the reaction zone 29 back to the heating zone 27.

For example, as illustrated in FIG. 3, the at least one fluidized bed reactor is a single one fluidized bed reactor 19 wherein the heating zone 27 is the bottom part of the fluidized bed reactor 19 while the reaction zone 29 is the top part of the fluidised bed reactor 19; with preference, the installation comprises one or more fluid nozzles 23 to inject a methane feedstock between the two zones (27, 29) or in the reaction zone 29. The fluidized bed reactor 19 further comprises optionally an inlet 7 for the material loading, optionally an outlet 9 for the material discharge and a gas outlet 11. With preference, the fluidized bed reactor 19 is devoid of heating means. For example, electrodes 13 are arranged at the bottom part of the fluidized bed reactor 19, i.e., in the heating zone 27. For example, the top part of the fluidised bed reactor 19, i.e., the reaction zone 29, is devoid of electrodes. Optionally, the fluidized bed reactor 19 comprises means 35 to transport the particles from the reaction zone 29 back to the heating zone 27; such as using a line arranged between the top part and the bottom part of the fluidized bed reactor 19.

For example, as illustrated in FIG. 4, the installation comprises at least two lateral fluidized bed zones (27, 29) connected one to each other wherein at least one fluidized bed zone 27 is the heating zone and at least one fluidized bed zone 29 is the reaction zone. For example, the heating zone 27 is surrounding the reaction zone 29. With preference, the installation comprises one or more fluid nozzles 23 arranged to inject a methane feedstock and optionally steam to the at least one reaction zone 29 using a distributor 33. The fluidized bed zones (27, 29) further comprise optionally an inlet 7 for the material loading and a gas outlet 11. With preference, the at least one fluidized bed zone being the heating zone 27 and/or the at least one fluidized bed zone being the reaction zone 29 is devoid of heating means. For example, the at least one fluidized bed zone being the reaction zone 29 shows optionally an outlet 9 for the material discharge. One or more fluid nozzles 21 provide a fluidizing gas to at least the heating zone from a distributor 31. Using one or more inlet devices 41, heated particles are transported from the heating zone 27 to the reaction zone 29 and using one or more means 35 comprising downcomers the separated particles are transported from the reaction zone 29 back to the heating zone 27. The fluidization gas for the heating zone 27 can be an inert diluent, like one or more selected from steam, air, methane, natural gas, hydrogen carbon dioxide, argon, helium and nitrogen. In such a configuration, the fluidization gas for the heating zone can also comprise air or oxygen to burn deposited coke from the particles.

For example, as illustrated in FIG. 5, the installation comprises at least two fluidized bed reactors (37, 39) connected one to each other wherein at least one fluidized bed reactor 37 is the heating zone 27 and at least one fluidized bed reactor 39 is the reaction zone 29. With preference, the installation comprises one or more fluid nozzles 23 arranged to inject a methane feedstock and optionally steam to the at least one fluidized bed reactor 39 being the reaction zone 29. The fluidized bed reactors (37, 39) further comprise optionally an inlet 7 for the material loading and a gas outlet 11. With preference, the at least one fluidized bed reactor 37 being the heating zone 27 and/or the at least one fluidized bed reactor 39 being the reaction zone 29 is devoid of heating means. For example, the at least one fluidized bed reactor 39 being the reaction zone 29 shows optionally an outlet 9 for the material discharge. Using the inlet device 41 heated particles are transported from the heating zone 27 to the reaction zone 29 when necessary and using device 35 the separated particles after the reaction zone are transported from the reaction zone back to the heating zone. The fluidization gas for the heating zone can be an inert diluent, like one or more selected from steam, air, methane, natural gas, hydrogen, carbon dioxide, argon, helium and nitrogen. In such a configuration the fluidization gas for the heating zone can also comprise air or oxygen to burn deposited coke from the particles.

For example, the at least one fluidized bed reactor 37 being the heating zone 27 comprises at least two electrodes 13 whereas the at least one fluidized bed reactor 39 being the reaction zone 29 is devoid of electrodes.

For example, the at least two fluidized bed reactors (37, 39) are connected one to each other by means 41 suitable to transport the particles from the heating zone 27 to the reaction zone 29, such as one or more lines.

For example, the at least two fluidized bed reactors (37, 39) are connected one to each other by means 35 suitable to transport the particles from the reaction zone 29 back to the heating zone 27, such as one or more lines.

The Methane-Comprising Feedstock

Any methane-containing feedstock can be used in the process of the disclosure but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide, ethane, propane and butanes in addition to methane. Ethane and other aliphatic hydrocarbons that may be present in the feed can be converted into substantially the same products during dehydrogenation step. Also, carbon dioxide is not disturbing for the reaction as it could mitigate coke formation.

Nitrogen and/or sulphur impurities are also typically present in methane-containing streams may be removed, or reduced to low levels, before use of the streams in the process. In an embodiment, the feed to the reactor contains less than 100 ppm, for example, less than 10 ppm, such as less than 1 ppm each of nitrogen and sulphur compounds.

In an embodiment, said feed stream contains carbon dioxide and comprises about 90 to about 99.9 mol. % of methane and about 0.1 to about 10 mol. % of $CO_2$. The feed used for dehydrogenation reaction could also comprise higher hydrocarbons than methane, including aromatic hydrocarbons. Such higher hydrocarbons can be recycled from the reactor effluent, added as separate co-feeds or can be present in the methane stream, such as, for example, when ethane, propane and/or butanes are present in a natural gas feed. Higher hydrocarbons recycled from the reactor effluent typically include one-ring aromatics and/or paraffins and olefins having predominately 6 or less, such as 5 or less, for example 4 or less, typically 3 or less carbon atoms. In a preferred embodiment, the feed contains less than 5 wt. % of C3+ hydrocarbons.

The Methane Pyrolysis Reaction

In the dehydrogenation reaction, the methane containing feedstock is contacted with hot particles of the fluidized bed to rupture C—H bonds. Depending on the products of interest, the fluidized bed might comprise of only conductive particles or of mixed conductive particles and catalyst particles. For example, if maximum hydrogen production and complete decomposition of methane into carbon is the goal, it is preferred to use more conductive particles.

In an embodiment, if the reaction aim is to produce ethylene and aromatics, it is preferred to use mixed conductive particles and catalyst particles.

Suitable conditions for the dehydrogenation reaction include a temperature ranging between 700° C. and 1100° C., preferably between 800° C. and 1050° C., more preferably between 900° C. and 1000° C.; and/or a pressure ranging between 0.1 MPa and 10.0 MPa, preferably between 1.0 MPa and 9.0 MPa.

EXAMPLES

Preparation of a Mo-Containing MFI Zeolite
  The starting materials used are as follow:
  Tetraehtylorthosilicate (TEOS), 98%, from Aldrich
  Tetrapropylammonium hydroxyl (TPAOH), 20 wt. % in water (1 M), from Alfa Aesar
  Sodium molybdate tetrahydrated ($Na_2MoO_4$, $2H_2O$), 98%, from Alfa Aesar
  Ammonium hepta-molybdate (($NH_4)_6Mo_7O_{24}$), from Alfa Aesar
  Sodium chloride (NaCl) from Alfa Aesar
  Lithium, sodium, potassium, or caesium vanadate (Li, Na, K, $CsVO_3$) from Aldrich
  Sodium stannate ($Na_2SnO_3$), 95%, from Aldrich
  Double distilled water
  These materials were used as received from manufacturers without any further purification.
  The zeolite samples described in the following examples are characterized by various methods as listed below:
Scanning Electron Microscopy (SEM):
  Scanning electron microscopy images of examples after a calcination step (h) were recorded using a MIRA\LMH (TESCAN) microscope, with an electron beam of 30 kV.
Powder X-Ray Diffraction (XRD):
  Powder samples of zeolites obtained after step (h) were measured using a PANalytical X'Pert Pro X-ray diffractometer equipped with a monochromator specific to CuKα radiation ($\lambda=1.5418$ Å, 45 kV, 40 mA). Samples were measured from 3 to 70° 2θ, with a step size of 0.016°. Le Bail profile refinement of each XRD patterns was also performed.
Solid-State Nuclear Magnetic Resonance of Silicon ($^{29}Si$ MAS NMR):
  Powder samples obtained after step (h) are packed into zirconia rotor of 4 mm outer diameter spun at 12 kHz, in a Bruker Avance III-HD 500 (11.7 T) spectrometer operating at 99.3 MHz. $^{29}Si$ MAS NMR spectra are recorded from a single pulse excitation (30° flip angle), used with a recycle delay of 30 s. {1H} $^{29}Si$ cross-polarization (CP) solid-state MAS NMR was acquired using a contact time of 5 ms and a recycle delay of 2 s. Chemical shifts were referenced to tetramethyl silane (TMS)
Raman Spectroscopy:
  Samples obtained after the calcination step (h) were measured using Raman spectrometry. The Raman spectra were collected on a Jobin Yvon Labram 300 confocal Raman spectrometer coupled to an optical microscope (objective 50×) and a CCD detector. A 532 nm wavelength laser was used, and spectra were accumulated 3 times for 60 s each. The power applied to the sample did not exceed 20 mW upon measurement.

Solid-State Nuclear Magnetic Resonance of Phosphorus ($^{31}$P MAS NMR):

Powdered sample obtained after the calcination step (h) and subsequently ion-exchanged to have the H-form, are analysed in $^{31}$P MAS NMR under $^{1}$H decoupling, using a phosphorus probe molecule: trimethylphosphine oxide (TMPO). All the following preparation steps are performed under Argon atmosphere to prevent the interaction of water with the probe molecule. The sample is first dehydrated, by heating at 400° C. for 4h under vacuum (av. $4.0 \times 10^{-5}$ Torr). In the meanwhile, a solution of TMPO dissolved in dichloromethane is prepared in anhydrous conditions. The solution is then added to the dehydrated sample. The as-obtained suspension is then subjected to sonication for 15 minutes, before the dichloromethane solvent is removed under vacuum, leaving the TMPO probe molecule impregnated into the zeolite sample. TMPO loaded sample is then packed into 4 mm outer-diameter zirconium rotor and analysed using $^{31}$P MAS NMR, performed on an 11.7 T Bruker Avance 500 spectrometer operating at a frequency of 500.0 MHz and 202.4 MHz for $^{1}$H and $^{31}$P respectively. A spinning rate of 14 kHz was used. $^{31}$P π/2 and π-pulses lengths were 7 and 14 μs respectively for all measurements.

Scanning Transmission Electron Microscopy with Energy Dispersive X-Ray Analysis (STEM/EDS) and High Angle Annular Dark Field Imaging (HAADF-STEM):

Experiments were performed on an Analytical double (objective and probe) corrected JEOL ARM200CF equipped with a 100 mm Centurio EDS detector and a Quantum GIF for the EELS. A probe of 0.1 nm was used to scan the sample in STEM mode and Bright Field and High Angle Annular Dark Field detectors were simultaneously employed for imaging. Camera length was 8 cm, and two different accelerating voltages of 200 and 80 kV were used in the STEM mode for imaging and chemical analysis respectively. Owing to the enhanced Z-contrast developed at 200 kV, this configuration was used for imaging and a high-speed scanning protocol (10 μsec/px) was employed to prevent sample degradation under the electron beam. To avoid such degradation, STEM-EDS analytical assays were carried out at 80 kV, with a scanning speed of 3 μs/px for a mean duration of 60 minutes. A cross-correlation algorithm implemented in the Jeol Analysis Station software was applied every 30 seconds in an effort to compensate for the special drift occurring during the test. The microstructure of samples was checked prior and after each EDS scan.

The Mo-containing MFI zeolite material has been synthesis according to the following steps (a) to (h):

Step (a)

In a polypropylene synthesis bottle (125 mL), a solution A is prepared by adding 8.197 g of TPAOH (1M) and 11.194 g of double-distilled water, under agitation performed using a magnetic stirrer. To this solution A is then added dropwise 6 g of TEOS, under stirring performed by a magnetic stirrer. The solution should be water clear and liquid. Upon preparation, the gel might be slightly inhomogeneous, but the solution should end up being water-like during the ageing step (beginning of step (b)).

Step (b):

The bottle containing the solution prepared in step (a) is air-tightly closed with a cap. The as-made synthetic suspensions are left for ageing under magnetic stirring for 1 h, and then on an orbital shaker for an additional 18h. All the steps up to this point are performed at a temperature between 10 and 35° C. and an ambient pressure between 0.9 and 1.2 Bar.

Step (c):

The synthesis mixture is water-like at this point. The synthetic mixture, still in its air-tightly closed bottle, is then subjected to static hydrothermal treatment at 90° C., for a duration of 5h.

Step (d):

The synthesis bottle is retrieved from step (c), and cooled down to room temperature under magnetic agitation, without opening the bottle. The synthesis mixture inside is still fully amorphous at this stage of the synthesis method. A solution B is prepared from 0.553 g of sodium molybdate di-hydrated $Na_2MoO_4 \cdot 2H_2O$ dissolved in 3 mL of double-distilled water. The solution is hand-shaken until it becomes water-clear. Solution B is then added drop-wise to the mixture that has just been cooled down, under vigorous magnetic stirring.

Step (e):

After full addition of the metal source, the bottle is closed again and left under magnetic stirring for an additional 1 h. The final overall molar gel composition (solution A and B mixed) is 1 $SiO_2$: 0.28 TPAOH: 0.08 $MoO_3$: 0.08 $M'_2O$: 40H2O.

Step (f):

The obtained synthesis mixture from step (e) is then placed in a static oven at 90° C. for 43 h.

Step (p):

The sample is removed from the oven after step (e) and cooled down to room temperature.

The solid phase is then separated from the liquid phase using centrifugation. The solid is dispersed in distilled water and centrifugation is performed again. This washing procedure is repeated until the pH of the liquid separated from the solid phase is around 7-8.

Step (h):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5h, holds at 550° C. for an additional 5h, before the furnace is allowed to cool down to room temperature in 5h. The as-obtained sample from step (h) is called MoMFI.

The invention claimed is:

1. A process to perform an endothermic methane pyrolysis reaction, said process comprising the steps of:
    a) providing at least one fluidized bed reactor comprising at least two electrodes, a bed comprising particles, and optionally a solid discharge system;
    b) putting the particles of the bed in a fluidized state by passing upwardly through the said bed a fluid stream, to obtain a fluidized bed;
    c) heating the fluidized bed to a temperature ranging from 500° C. to 1200° C. to conduct the endothermic methane pyrolysis reaction to produce a reactor effluent comprising at least solid carbon, one or more hydrocarbons having at least two carbons and hydrogen;
    d) optionally recovering from the reactor effluent produced at step (c) the one or more hydrocarbons having at least two carbons and hydrogen;

characterized in that the particles of the bed comprise electrically conductive particles and particles of a catalytic composition, wherein at least 10 wt. % of the particles of the bed are electrically conductive particles and have a resistivity ranging from 0.001 Ohm·cm to 500 Ohm·cm at 800° C., wherein the catalytic composition comprises a catalytic support and one or more metallic compounds selected from the group consisting of Ca, Mg, Ba, Y, La, Sc, Ce, Ti, Zr, Hf, V, Nb, Ta, Cr, Mo, W, Mn, Re, Fe, Ru, Co, Rh, Ir, Ni, Pd, Cu, Ag, Au, Zn, Al, Ga, Si, Ge, In, Sn, Pb, and Bi;

in that from 50 wt. % to 100 wt. % of the electrically conductive particles of the bed are or comprise one or more selected from the group consisting of one or more metallic alloys, one or more non-metallic resistors, one or more metallic carbides, one or more transition metal nitrides, one or more metallic phosphides, graphite, carbon black, and any mixture thereof;

in that the void fraction of the bed is ranging from 0.5 to 0.8; and in that the step (c) of heating the fluidized bed is performed by passing an electric current through the fluidized bed.

2. The process according to claim 1, characterized in that the electrically conductive particles of the bed are or comprise one or more non-metallic resistors selected from the group consisting of silicon carbide, molybdenum disilicide and a mixture thereof.

3. The process according to any claim 1, characterized in that the electrically conductive particles of the bed are or comprise a mixture of a non-metallic resistor being silicon carbide and electrically conductive particles different from silicon carbide that are graphite, characterized in that the electrically conductive particles of the bed comprise from 10 wt. % to 99 wt. % of silicon carbide based on the total weight of the electrically conductive particles of the bed.

4. The process according to claim 1, characterized in that, wherein the at least one fluidized bed reactor provided in step a) comprises a heating zone and a reaction zone and wherein the fluid stream provided in step b) is provided to the heating zone and comprises diluent gases, the step c) of heating the fluidized bed to a temperature ranging from 500° C. to 1200° C. to conduct the endothermic methane pyrolysis reaction comprises the following sub-steps:

heating the fluidized bed to a temperature ranging from 500° C. to 1200° C. by passing an electric current through the heating zone of the at least one fluidized bed, transporting the heated particles from the heating zone to the reaction zone, in the reaction zone, putting the heated particles in a fluidized state by passing upwardly through the said bed of the reaction zone a fluid stream comprising a methane feedstock and optional diluent gases to obtain a fluidized bed and to conduct the endothermic methane pyrolysis reaction on the methane feedstock, and recovering the particles from the reaction zone and recycling them to the heating zone.

5. The process according to claim 1, characterized in that the electrically conductive particles of the bed comprise one or more metallic alloys selected from the group consisting of Ni-Cr, Fe-Ni—Cr, Fe-Ni—Al and a mixture thereof.

6. The process according to claim 1, characterized in that the one or more metallic compounds of the catalytic composition are selected from Fe, Mo, W or Re.

7. The process according to claim 1, characterized in that the one or more metallic compounds of the catalytic composition are selected from the group consisting of an elemental, a metal oxide, carbide, sulphide, nitride, and phosphide form.

8. The process according to claim 1, characterized in that the one or more metallic compounds of the catalytic composition are deposited on the catalyst support in an amount ranging from 0.1 wt. % to 20.0 wt. % based on the total weight of said catalyst composition, characterized in that said catalytic support is selected from the group consisting of carbon materials, one or more zeolites selected from the group consisting of AEL, AFI, AFO, BEA, CHA, ERI, FAU, FER, ITE, ITH, IWR, IWS, IWW, KFI, LEV, LTL, MEL, MFI, MFS, MOR, MSE, MTT, MTW, MWW, TON and VFI families, $Al_2O_3$, and one or more mesoporous materials and is present in an amount of at least 60 wt. % based on the total molar content of the catalyst composition; characterized in that when said catalytic support is said one or more zeolites, said one or more zeolites are subjected to a step of steaming before step (c).

9. The process according to claim 8, characterized in that said catalytic support is one or more zeolites, and said one or more zeolites comprise a molar ratio of silicon over the sum of the amount of the aluminium and the metallic element of at least 5.

10. The process according to claim 8, characterized in that said catalytic support is one or more zeolites; and said one or more zeolites are selected from the MFI family, or that said one or more zeolites have a crystalline alumino-silicate oxide framework substituted with a metal selected from the group consisting of Fe, Sn, Hf, Zn, Zr, Ti, V, Ta, Ga, Ge, Nb, Mn, Mo, W, Co, and Cd.

11. The process according to claim 1, characterized in that the content of the particles of the catalytic composition based on the total weight of the particle of the bed ranges from 10 wt. % to 100 wt. %.

* * * * *